United States Patent [19]
Lane et al.

[11] Patent Number: 5,908,940
[45] Date of Patent: *Jun. 1, 1999

[54] PROCESSES FOR RECOVERING TOCOTRIENOLS, TOCOPHEROLS AND TOCOTRIENOL-LIKE COMPOUNDS

[75] Inventors: Ronald H. Lane, Phoenix, Ariz.; Kenneth W. Becker, Topeka, Kans.; Asaf A. Qureshi, Madison, Wis.; D. Michael Wells, Abbeyville, La.

[73] Assignee: Lipogenics, Inc., Scottsdale, Ariz.

[ * ] Notice: This patent is subject to a terminal disclaimer.

[21] Appl. No.: 08/583,232

[22] Filed: Jan. 5, 1996

Related U.S. Application Data

[63] Continuation-in-part of application No. 07/952,615, Jan. 19, 1993, which is a continuation of application No. PCT/US91/03626, May 23, 1991, which is a continuation-in-part of application No. 07/527,612, May 23, 1990, abandoned, said application No. 08/583,232, Jan. 5, 1996, is a continuation-in-part of application No. 08/244,215, Aug. 15, 1994, Pat. No. 5,591,772, which is a continuation of application No. PCT/US92/10277, Nov. 20, 1992, which is a continuation-in-part of application No. 07/796,486, Nov. 19, 1991, abandoned.

[51] Int. Cl.$^6$ .................................................. C07D 311/72
[52] U.S. Cl. .......................................... 549/413; 549/408
[58] Field of Search ..................................... 549/413, 408

[56] References Cited

U.S. PATENT DOCUMENTS

| | | | |
|---|---|---|---|
| 2,203,400 | 6/1940 | Andrews | 549/413 |
| 3,122,565 | 2/1964 | Kijima et al. | 260/345.6 |
| 3,317,564 | 5/1967 | Ruegg et al. | 260/345.5 |
| 3,369,305 | 2/1968 | Becker | 34/22 |
| 3,869,477 | 3/1975 | Shindo et al. | |
| 4,034,083 | 7/1977 | Mattson | |
| 4,088,778 | 5/1978 | Igarashi et al. | |
| 4,122,094 | 10/1978 | Woziwodzki | |
| 4,285,951 | 8/1981 | Hoefle | |
| 4,603,142 | 7/1986 | Burger et al. | |
| 4,788,304 | 11/1988 | Marshall et al. | 549/549 |
| 4,808,426 | 2/1989 | Strop et al. | |
| 5,047,254 | 9/1991 | Lee | 426/417 |
| 5,138,075 | 8/1992 | Ohgaki et al. | 549/413 |
| 5,591,772 | 1/1997 | Lane et al. | 549/408 X |

FOREIGN PATENT DOCUMENTS

| | | | |
|---|---|---|---|
| 480484 | 1/1952 | Canada | 549/413 |
| 484880 | 7/1952 | Canada | 549/413 |
| 494635 | 7/1953 | Canada | 549/413 |
| 2090836 | 7/1982 | United Kingdom | C07D 311/72 |
| 2117381 | 10/1983 | United Kingdom | C07D 311/72 |
| 2135672 | 9/1984 | United Kingdom | C07D 311/72 |
| PCCT/US91/03626 | 5/1991 | WIPO | |
| PCT/US92/10277 | 11/1992 | WIPO | |

OTHER PUBLICATIONS

Guzman et al., "Properties of Soybean–Corn Mixtures Processed by Low–Cost Extrusion," J. Food. Sci., 54(6), pp. 1590–1593 (1989).

Hargrove, Jr., "Rice Bran in Bakery Food," AIB Res. Dept. Technical Bulletin, 12(2), p. 1 (1990).

Takatsuji, "Production of Whole Fat Soybean Flour," Patent Abstracts of Japan, 9(247), Abstract No. C307 (1985).

Tan et al., "Separation of Tocopherol and Tocotrienol Isomers Using Normal—and Reverse–Phase Liquid Chromatography," Anal. Biochem., 180, pp. 368–373 (1989).

Watabe et al., "Simultaneous Determination of Zeranol, 17—Estradiol andDiethylstilbesterol in Beef by HPLC with Amperometric Detection Using Column Switching," Chemical Abstracts, 112(7), Abstract No. 5387a (1990).

*Primary Examiner*—Michael G. Ambrose
*Attorney, Agent, or Firm*—Lyon & Lyon LLP

[57] ABSTRACT

The present invention relates to processes for obtaining Tocol products, such as tocotrienols, tocopherols and tocotrienol-like compounds from plant sources in high yields. More particularly, this invention relates to processes for stabilizing and recovering Tocol products from plant materials, such as cereals, grains and grain oils. The Tocol products recovered according to this invention are useful in pharmaceutical compositions, food formulations and dietary supplements. These compositions, formulations and supplements advantageously lower the blood level of low density lipoproteins and total serum cholesterol in humans and animals.

15 Claims, 19 Drawing Sheets

PROCESSES FOR RECOVERING TOCOTRIENOLS, TOCOPHEROLS AND TOCOTRIENOL-LIKE COMPOUNDS

This application is a continuation-in-part of copending U.S. application Ser. No. 07/952,615, filed Jan. 19, 1993, which prior application resulted from a filing under 35 U.S.C. §371 of PCT/US91/03626, filed May 23, 1991, which is in turn a continuation-in-part of U.S. application Ser. No. 07/527,612, filed May 23, 1990, now abandoned. This application is also a continuation-in-part of U.S. application Ser. No. 08/244,215, filed Aug. 15, 1994, now U.S. Pat. No. 5,591,772, which prior application resulted from a filing under 35 U.S.C. §371 of PCT/US92/10277, filed Nov. 20, 1992, which is in turn a continuation-in-part of U.S. application Ser. No. 07/796,486, filed Nov. 22, 1991, now abandoned. All of the above applications are expressly incorporated herein.

FIELD OF THE INVENTION

The present invention relates to processes for obtaining Tocol products, such as tocotrienols, tocopherols and tocotrienol-like compounds from biological sources in high yields. More particularly, this invention relates to processes for stabilizing and recovering Tocol products from plant materials, such as cereals, grains and grain oils. The Tocol products recovered according to this invention are useful in pharmaceutical compositions, food formulations and dietary supplements. These compositions, formulations and supplements advantageously lower the blood level of low density lipoproteins and total serum cholesterol in humans and animals.

BACKGROUND OF THE INVENTION

Hypercholesterolemia is a causative agent of diseases including arteriosclerosis, atherosclerosis, cardiovascular disease and xanthomatosis. In addition, high serum cholesterol levels are seen in patients suffering from diseases including diabetes mellitus, various liver disorders, such as hepatitis and obstructive jaundice, familial hypercholesterolemia, acute intermittent prothyria, anorexia nervosa, nephrotic syndrome and primary cirrhosis. Improvement of lipoprotein profiles has been shown to retard the progression of such diseases, as well as to induce regression of clinically significant lesions in hypercholesterolemic patients.

To date, several classes of therapeutic agents have been used in the treatment of hypercholesterolemia. The first class of therapeutics, directed at reducing cholesterol absorption from the blood, include cholestyramine, colestipol, colchicine, neomycin, kanamycin, chloramphenicol, chlortetracycline and β-sitosterol. The utility of such compounds is often limited by serious and frequent side effects, including aberrations in digestive function and malabsorption of essential nutrients. Furthermore, these drugs often induce a decrease in cholesterol absorption and an increase in cholesterol biosynthesis which, in turn, may effectively prevent or lessen the degree of total serum cholesterol reduction.

Agents which block the biosynthesis of cholesterol constitute another class of hypocholesterolemic drugs. Such compounds include mevinolin, synvinolin, eptastin, CPIB, atromid, methyl clofenapate, Su-13,437, halogenate, benzmalacene, DH-581 and MER-29. The administration of these synthesis blockers often leads to a toxic build-up of cholesterol precursors in blood and tissues.

Other classes of drugs used to treat hypercholesterolemia include those which act upon plasma lipoproteins (i.e., nicotinic acid), bile acid kinetics (i.e., choleic acid), β-adrenergic receptors (i.e., propranolol), endocrine systems (i.e., growth hormones) and those with yet undetermined modes of action (i.e., pyridoxine and inositol).

The reduction of cholesterol level achieved by any of these classes of drugs is variable and rarely exceeds 25%, while the incidence of side effects may significantly limit their use.

As an alternative to pharmaceutical treatment of hypercholesterolemia, surgical procedures, such as partial ileal bypass and manipulation of the digestive tract, have been employed (J. Sabine, *Cholesterol*, pp. 237–40, Marcel Dekker Inc., New York (1977)). Attendant with such treatments, however, are the risks associated with invasive procedures. Although exercise regimens and dietary intake restrictions have been shown to reduce cholesterol levels, patient compliance with these types of therapy is often sporadic or insufficient to effect clinical improvement.

There is a low incidence of cardiovascular disease in populations consuming large amounts of cereal grains. Soluble and insoluble fibers have, in the past, been viewed as the agents responsible for cholesterol reduction in such populations (see D. Kritchevsky et al., "Fiber, Hypercholesterolemia and Atherosclerosis", *Lipids*, 13, pp. 366–69 (1978)). More recently, however, the hypocholesterolemic effects of cereal grains have been attributed to natural components of the grains—tocotrienols ("$T_3$") and structurally similar compounds, such as tocopherols ("T"). For example, in U.S. Pat. No. 4,603,142, d-α-tocotrienol, isolated from barley extracts, was identified as an inhibitor of cholesterol biosynthesis. See also A. Qureshi et al., "The Structure of an Inhibitor of Cholesterol Biosynthesis Isolated From Barley", *J. Biol. Chem.*, 261, pp. 10544–50 (1986)). Tocotrienols and tocopherols occur naturally in small quantities in plant sources, such as rice bran, palm oil and barley.

Tocotrienols are of special interest as cholesterol lowering agents, because they decrease the blood level of the low density lipoprotein fraction of cholesterol (LDL-cholesterol) and total serum cholesterol level, while increasing the ratio of the high density lipoprotein fraction of cholesterol (HDL-cholesterol) to LDL-cholesterol. Such effects are clinically significant, because HDL-cholesterol beneficially lowers the risk of heart disease (T. Gordon et al., "High Density Lipoprotein as a Protective Factor Against Coronary Heart Disease", *The American Journal of Medicine*, 62, pp. 707–14 (1977)).

Efforts to extract tocotrienols and tocotrienol-like compounds, such as tocopherols, from various grains, cereals and oils have resulted in the recovery of relatively small amounts of the desired compounds. For example, Canadian patent 480,484 refers to a method for preparing small amounts of tocopherol concentrates from a by-product of animal and plant oil processing called scum. Yields of tocopherols and tocotrienols according to United Kingdom patent application 2,090,836 are also low. It is believed that enzymes present in biological sources typically destroy tocopherols, tocotrienols and tocotrienol-like compounds during milling, extraction and other conventional processing techniques (see A. Qureshi et al., supra).

Accordingly, the need exists for processes which stabilize biological sources, thereby providing biological sources characterized by an increased content of tocotrienols, tocopherols and tocotrienol-like compounds and facilitating the isolation of tocotrienols, tocopherols and tocotrienol-like compounds from those sources in high yields.

SUMMARY OF THE INVENTION

The present invention solves the problems referred to above by providing processes for recovering T, $T_3$ and $T_3$-like compounds ("collectively referred to as Tocol products") from biological sources in high yields. By virtue of the present invention, crude biological materials containing Tocol products are treated to yield natural T, $T_3$ and T-like compounds, and Tocol-rich products containing them, in commercially feasible amounts, for a variety of uses. By virtue of the processes of this invention, the content of Tocol products in a biological source is enhanced.

The processes of this invention are characterized by a dry heat stabilization stage which stabilizes the biological source. According to one embodiment, this invention is characterized by a two-stage stabilization process, comprising a first dry heat stabilization step, followed by a second wet heat stabilization step.

The processes of this invention advantageously provide biological materials stabilized against enzymes, such as lipases, peroxidases, polyphenol oxidases, lipoxygenases and catalases, which would otherwise degrade the T, $T_3$ and $T_3$-like compounds contained therein. Furthermore, the processes of this invention facilitate the release of the T, $T_3$ and $T_3$-like compounds contained in the biological source yet constrained therein by interactions, such as hydrogen bonds, covalent bonds, ionic bonds and hydrophobic interactions. And the processes of this invention increase the solubility of the $T_1$, $T_3$ and $T_3$-like compounds contained in the biological source.

Accordingly, T, $T_3$ and $T_3$-like compounds are present in and may be recovered from biological materials stabilized according to this invention in higher amounts than those obtained using conventional techniques for processing biological materials or extracting Tocol products therefrom. Such stabilized natural materials, and the natural products recovered therefrom, are useful in the treatment and prevention of diseases attributed to high blood levels of LDL-cholesterol and total serum cholesterol. More particularly, the Tocol-rich products of the present invention are useful in pharmaceutical compositions, food formulations and dietary supplements to lower blood levels of LDL-cholesterol and total serum cholesterol, while increasing the ratio of HDL-cholesterol to LDL-cholesterol in the blood.

DETAILED DESCRIPTION OF THE INVENTION

Figure 1:
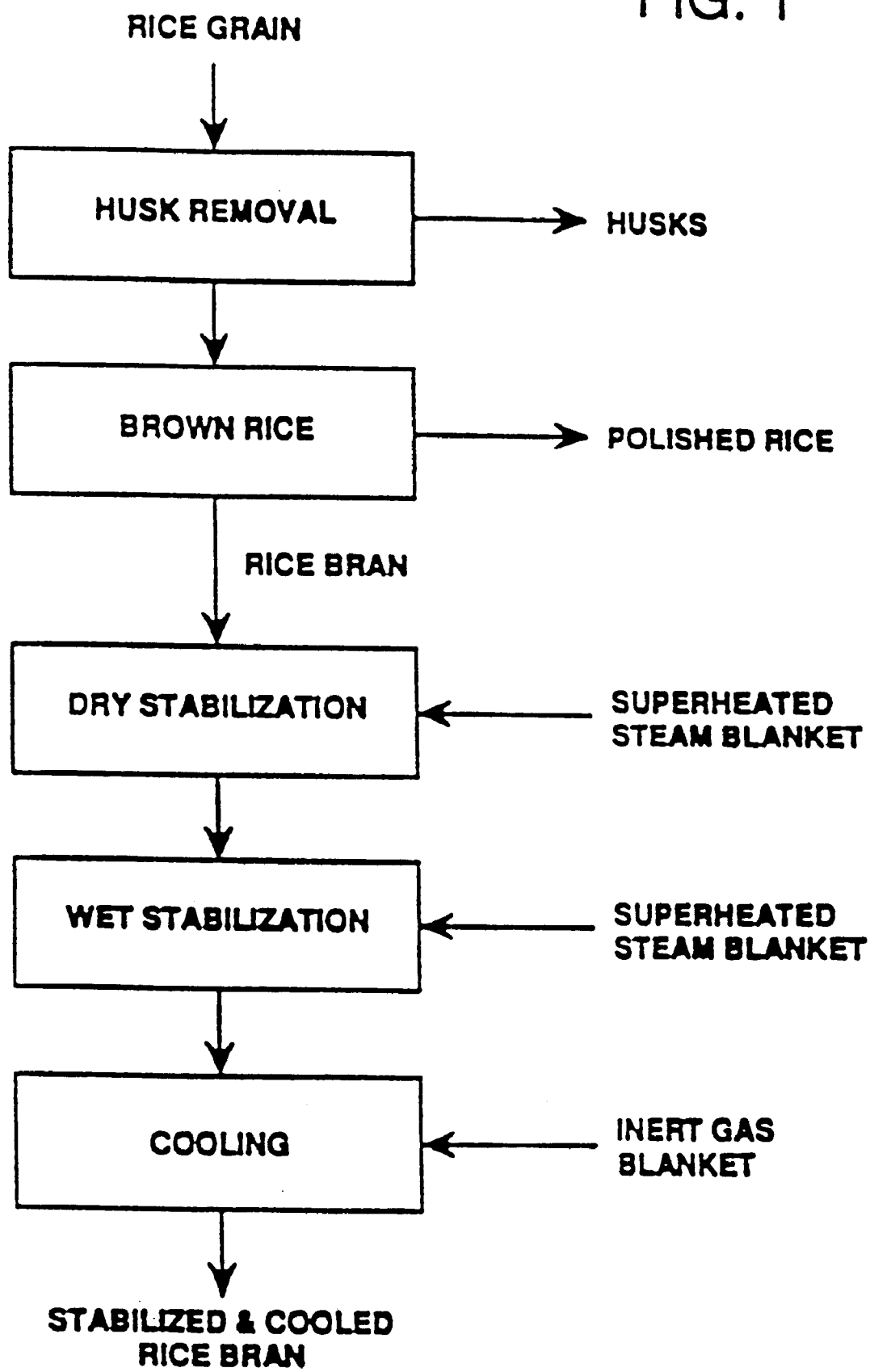
FIG. 1 is a schematic of one embodiment of the processes of the present invention for preparing Tocol-rich stabilized and cooled rice bran from whole rice grain.

In order that the invention herein described may be more fully understood, the following detailed description is set forth. In the description, the following terms are employed:

Biological source—Any natural or recombinant plant source, microbial source (e.g., bacteria), fungi, yeast, algae, higher plant source, or derivative thereof, which contains tocopherols (T), tocotrienols ($T_3$) or tocotrienol-like ($T_3$-like) compounds and which may be effectively stabilized by the processes of the present invention.

Stabilization—A process effective to enhance the content of tocopherols (T), tocotrienols ($T_3$) or tocotrienol-like compounds ($T_3$-like compounds) in a biological source by one or a combination of: (1) inactivating enzymes which are capable of degrading T, $T_3$ and $T_3$-like compounds in that biological source or (2) breaking bonds or otherwise interfering with interactions—such as hydrogen bonds, covalent bonds, ionic bonds and hydrophobic interactions which bind the desired products to proteins, sugars, lipids, carbohydrates, membranes, glycoproteins, or combinations thereof, in the biological source—which retain T, $T_3$ and $T_3$-like compounds in that biological source, thus facilitating the release of those desired compounds, or (3) increasing the solubility of the T, $T_3$ and $T_3$-like compounds of that biological source beyond that prior to stabilization or beyond the level of solubility of the T, $T_3$ and $T_3$-like compounds of a corresponding non-stabilized biological source or of a corresponding non-stabilized biological source treated according to conventional heat treatment processes or conventional stabilization processes. As a result of stabilization, the content of T, $T_3$ and $T_3$-like compounds in a biological source is enhanced. Advantageously, therefore, T, $T_3$ and $T_3$-like compounds may be recovered from the stabilized biological source in higher yields than those realized from a corresponding non-stabilized biological source or a corresponding non-stabilized biological source treated according to conventional heat treatment processes or conventional stabilization processes. In a preferred embodiment of this invention, stabilization is effected by treating the biological source with heat.

Tocol or Tocol Products—A mixture of one or more compounds selected from tocopherols (T), tocotrienols ($T_3$) and tocotrienol-like ($T_3$-like) compounds.

Tocotrienol-like—Any biologically active compound which is contained in a biological source and (1) which is released, or whose release is facilitated, upon stabilizing that source or (2) whose content in that source is enhanced by stabilizing that source. Such tocotrienol-like compounds include any biologically active compound displaying the biological activity of a tocotrienol which inhibits the synthesis of HMGR as measured by an in vitro HMGR assay, such as that described in A.G. Gornall et al., *J. Biol. Chem.*, 177, pp. 751–66 (1949). Tocotrienol-like compounds include, but are not limited to, trienols that are not tocotrienols and enols that are not trienols, any electron transfer ring compounds, anti-oxidant type compounds and compounds similar to or containing the tocotrienol side chain. Specific examples of $T_3$-like compounds are ubiquinones, plastoquinones, isoquinones, phylloquinones, unsaturated terpenoids and cyclic and acyclic, saturated and unsaturated isoprenoids.

TRF—A tocotrienol-rich fraction obtained by the stabilization of a biological source. It is characterized by an elution profile on HPLC of the recovered oils on silica columns (C 18 columns) using a hexane and isopropanol (99.7%:0.3%) eluant for an elution time of about 0.01 to 120 minutes. Detection is carried out by fluorescence monitoring at 295 nm and 330 nm or by monitoring at 280 UV to 295 UV.

Tocol-Rich Product—(1) A stabilized biological source containing Tocol products or (2) Tocol products recovered from a stabilized biological source.

Enhanced—The Tocol content is increased beyond than that of the biological source prior to stabilization and, therefore, (1) Tocol products may be recovered from the stabilized source in higher yields than those realized from a corresponding non-stabilized source or a corresponding non-stabilized source treated according to conventional heat treatment or stabilization processes or (2) Tocol products may be more soluble than they were prior to stabilization or more soluble than those of a corresponding non-stabilized source or more soluble than those of a non-stabilized biological source treated according to conventional heat treatment or stabilization process.

The processes of the present invention permit the stabilization of biological sources containing T, $T_3$ and $T_3$-like compounds, so that the content of those Tocol products in the source is enhanced. As a result, T, $T_3$ and $T_3$-like compounds may be recovered from those stabilized sources in high yields. According to one embodiment of this invention, biological materials are treated by dry heat, using reaction conditions which stabilize the materials without destroying the desired T, $T_3$ and $T_3$-like compounds present therein. In a preferred embodiment for rice bran, or another material having high peroxidase content or a high degree of fines, following this dry heat stabilization step, the biological materials are subjected to a wet heat stabilization step, preferably carried out in sequence in the same apparatus as that used for the dry heat stabilization, under reaction conditions effective to further stabilize the materials without destroying the desired T, $T_3$ and $T_3$-like compounds.

Following stabilization, the Tocol-rich biological materials may be extracted and the Tocol products recovered therefrom in higher yields than those realized from non-stabilized materials or materials subjected to conventional heat treatment or conventional stabilization processes. In turn, these materials may be processed using conventional methods such as, desolventization, deodorization, degumming, bleaching and refining, to yield an edible, extracted food product. Alternatively, the Tocol-rich products are retained in the biological materials, which are then processed for consumption.

The processes of this invention may be used to treat all types of biological materials including, but not limited to, oats, wheat, rye, barley, brewers' grain, soybean, wheat germ, wheat bran, corn, rice, cottonseed, flax, sesame, amaranth, rice bran, parboiled brown rice, brown rice flour, spit brewers' malt, vegetable oil distillant, fruit concentrate evaporate, barley bran, palm oil, wheat germ oil, rice bran oil, brewers' grain oil, barley oil, coconut oil, cottonseed oil, soybean oil, other plant malts, other cereal grains and other cereal grain oils, plant tissues, leaves, stems, bark, roots, nuts and legumes, or portions thereof. Preferably, the biological source is rice bran.

Advantageously, the biological source containing the T, $T_3$ and $T_3$-like compounds need not be subjected to any particular mechanical, chemical or enzymatic pre-treatment in order to permit recovery of those desired products. Optionally, however, materials to be treated may be produced, prepared or pre-treated by employing conventional techniques. Such techniques should be those which do not destroy the content of T, $T_3$ or $T_3$-like compounds in the biological materials.

In accordance with this invention, stabilization of biological materials is carried out using a combination of parameters including temperature and time of exposure, and optionally, in preferred embodiments, further including parameters of pressure and/or moisture in the stabilization apparatus.

Generally, during the dry heat or wet heat stabilization stage, conditions are as follows. The pressure should be in the range of about −30 inches Hg to about 10,000 PSI. The preferred pressure for dry heat stabilization is about 2,000 PSI and the preferred pressure for wet heat stabilization is between about 800 and about 2,000 PSI. The temperature should be in the range of about 0° C. to about 500° C. The preferred temperature for dry heat stabilization is in the range of about 80° C. to about 500° C., more preferably in the range of about 80° C. to about 350° C., more preferably in the range of 150° C. to 250° C., and more preferably still, greater than 200° C., and including the range of 201° C. to 500° C. and the range of 201° C. to 350° C. The preferred temperature for wet heat stabilization is between about 100° C. and about 150° C.

The treatment time should be in the range of about 1 second to about 4 hours. The preferred treatment time for dry heat stabilization is, depending on the heating conditions, between about 20 seconds and about 4 hours, more preferably between about 1 minute and about 4 hours, more preferably between about 90 seconds and about 4 hours, more preferably between about 5 minutes and about 4 hours, more preferably between about 10 minutes and about 4 hours, more preferably between about 30 minutes and about 4 hours. The preferred treatment time for wet heat stabilization is between about 10 and about 60 seconds. Moreover, where the stabilization temperature is to be 200° C. or lower, then the treatment time should be for longer than 30 seconds, and up to 4 hours, more preferably between about 90 seconds and about 4 hours, more preferably between about 5 minutes and about 4 hours, more preferably between about 10 minutes and about 4 hours, more preferably between about 30 minutes and about 4 hours.

The moisture level should be in the range of about 1% to about 95%—i.e., the moisture level of the biological material is between about 1% and about 95% by weight. The preferred moisture level for dry heat stabilization is between about 5% and the preferred moisture level for wet heat stabilization is between about 15% and about 30%. It should be understood, however, that the specific choice within a range for a given parameter will depend upon one or more of the other parameters chosen, as well as the type of biological material to be stabilized.

As will be appreciated by a person of ordinary skill in the art, these parameters may by varied in concert from the ranges exemplified herein, while still providing a stabilized biological material. For example, if a desired temperature for stabilization is lower than the range specifically set forth herein, it may be employed in combination with a pressure, treatment time or moisture level greater than those illustrated, in order to stabilize a biological material. Accordingly, the present invention also includes various combinations of the four parameters of temperature, pressure, treatment time and moisture other than those illustrated herein, as long as those combinations result in the production of a stabilized biological material. This invention also contemplates combinations of less than all of these four parameters, as long as those combinations yield a stabilized biological material. The only constraints on such combinations are that the temperature, pressure, treatment time and moisture, or the combination thereof, should not be increased to a level which would result in destruction of the desired Tocol products, decomposition of the non-Tocol containing byproducts or unwanted side reactions, such as oxidizing pyrolytic or Maillard reactions. It should also be understood that the optimal treatment conditions for stabilization will depend on factors such as the type and volume of biological material to be treated and the form of the desired end product.

Any form of heat may be used to effect stabilization of the biological material. Accordingly, stabilization may be carried out using any conventional extruder, crop cooker, microwave, polarized microwave or other heating oven or cooker equipment. The choice of specific equipment may vary, depending upon the desired production scale, type of biological material to be treated, throughput, time scale, moisture content, operating environment and availability of electricity, steam and gas. Typically, stabilization may be carried out in any vessel in which provision has been made for the desired temperature, pressure, oxygenation, agitation, moisture and treatment time for the particular biological material. According to preferred embodiments of this invention, stabilization of a biological material is carried out in an Anderson extruder, a Wenger extruder or a polarized microwave apparatus. The use of heat as the agent for stabilizing biological materials may accelerate the oxidation of the desired T, $T_3$ and $T_3$-like compounds present in those materials. Accordingly, heat treatment should preferably be carried out under conditions that minimize or eliminate oxidative effects. Such conditions include the creation of a pressurized vacuum or the use of superheated steam, an inert gas or the evacuation of air in the heating equipment.

Following stabilization, the biological material is characterized by an increased content of Tocol products relative to the content of Tocol products in the starting material—i.e., it is a Tocol-rich product. The total Tocol content of the stabilized biological material is typically increased about 100% over that of the non-stabilized starting material. The Tocol content, measured in ppm, may be determined by conventional methods, such as those described in V. Piironen et al., "High Performance Liquid Chromatographic Determination Of Tocopherols And Tocotrienols And Its Application To Diets And Plasma Of Finnish Men," *Internat. J. Vit. Nutr. Res.*, 53, pp. 35–40 (1984) and B. Tan et al., "Separation Of Tocopherol And Tocotrienol Isomers Using Normal- And Reverse-Phase Liquid Chromatography," *Anal. Biochem.*, 180, pp. 368–373 (1989).

In a preferred embodiment of this invention, the biological source is a plant material. Typically, the plant materials to be treated in the processes of this invention are first selected and then harvested. Preferably, the plant source chosen contains low concentrations of enzymes, such as lipases, peroxidases, catalases, polyphenol oxidases and lipoxygenases, which may begin to degrade the Tocol products once the outer husk of the plant source is removed in the milling process. The concentration of these enzymes in the plant source may be determined, for example, using tributyrin under $N_2$, at pH 7.5 and 35° C.

After harvesting, the plant source is subjected to the process steps illustrated in FIG. 1 for preparing Tocol-rich stabilized rice bran from rice whole grain, the most preferred plant source. Preferably, the stabilization process is initiated within as short a time as possible after harvesting, so that enzymes in the unstabilized plant source do not begin to degrade the desired Tocol products. As shown in FIG. 1, the first step for plant sources such as, for example, rice, wheat, rye, oats, flax, sesame and amaranth, is to remove the husk, bran coat and germ from the grain or seed by milling. For example, after removal of husks from whole rice grain, bran is then removed to provide white rice and rice bran products.

Following milling, enzymes present in unstabilized plant sources, such as lipases, peroxidases, catalases, polyphenol oxidases and lipoxygenases, may become active. In activated form, these enzymes cause the undesired alteration or destruction of the T, $T_3$ and $T_3$-like components of the plant material. According to a preferred embodiment of this invention, therefore, plant materials are subjected to stabilization in one or two stages, immediately after milling. In each stage, stabilization is carried out under conditions effective to do one or more of the following: (1) inactivate enzymes capable of destroying the Tocol products contained in the plant material, or (2) break bonds or otherwise interfere with interactions which retain T, $T_3$ and $T_3$-like compounds in the material, or (3) increase the solubility of the T, $T_3$ and $T_3$-like compounds of that biological source beyond that prior to stabilization or beyond the level of solubility of the T, $T_3$ and $T_3$-like compounds of a corresponding non-stabilized biological source or of a corresponding non-stabilized biological source treated according to conventional heat treatment processes or conventional stabilization processes.

When active, enzymes which are capable of destroying the Tocol products contained in the plant material also cause a rapid build-up of free fatty acids (FFA) which in turn, can destroy $T_3$ and possibly the $T_3$-like compounds via a radical mechanism. The yield of T, $T_3$ and $T_3$-like compounds is optimized when the FFA content in the plant material is reduced to about 4% or less. Preferably, the FFA content is zero. FFA content may be monitored using the official AOCS method Ca Sa-40. Preferably, the FFA content in the plant material after stabilization is the same as that prior to stabilization. Immediate processing of the plant source after milling provides a stabilized product with a low FFA content and a high concentration of T, $T_3$ and $T_3$-like compounds.

The dry heat stabilization step typically inactivates lipases and other hydrolytic enzymes in the plant source. The subsequent wet stabilization stage primarily inactivates peroxidases and other oxidative enzymes in the plant source, as well as any other enzymes which become regenerated during storage of the plant source for a time between the dry heat stabilization stage and the wet heat stabilization stage.

The dry heat stabilization step may be carried out in any apparatus that accommodates the desired parameters of temperature, moisture, treatment time and pressure required to inactivate Tocol-destroying enzymes, to permit or facilitate the release of Tocol products from the plant source or to increase the solubility of the Tocol products. During the dry heat stabilization stage, FFA build-up increases with stabilization temperature. Therefore, lower temperatures and a short residence time in the apparatus are preferred. In one embodiment of this invention, a plant source is preferably dry stabilized in an extruder under the preferred parameters of temperature, treatment time, moisture and pressure. Some plant materials, such as grains and cereals, are preferably subjected to microwaving, or other heating, before or after extrusion, to increase the extraction rate and decrease the residence time in the heat providing apparatus, thereby facilitating recovery of the desired Tocol products. Microwaving before or after extrusion may also aid in rupturing the cells of the plant source and minimizing enzymatic destruction or undesirable alteration of the Tocol products.

Since T, $T_3$ and $T_3$-like compounds present in plant sources are highly susceptible to oxidation during stabilization, a blanket of superheated steam, an inert gas, such as $N_2$, or a vacuum is used to protect the plant source from oxygen and, therefore, to prevent high peroxide value (PV) from developing. Superheated steam is preferred, because it is readily available and can also serve as an even source of heat in the apparatus. During stabilization, PV may be monitored using official AOCS method Cd 8–53.

When the plant material to be stabilized is rice bran, or another material having high peroxidase content or a high degree of fines, following the dry heat stabilization step, the plant material is preferably further stabilized in a wet heat stabilization step carried out under the preferred parameters of temperature, treatment time, moisture and pressure for wet heat stabilization. This wet heat stabilization step further reduces any residual enzyme activity that may cause destruction of T, $T_3$ and $T_3$-like products in the stabilization apparatus. Additionally, the wet heat stabilization step may break bonds or otherwise interfere with interactions which retain T, $T_3$ and $T_3$-like compounds in the plant material or it may increase the solubility of the T, $T_3$ and $T_3$-like compounds of that biological source beyond that prior to stabilization or beyond the level of solubility of the T, $T_3$ and $T_3$-like compounds of a corresponding non-stabilized biological source or of a corresponding non-stabilized biological source treated according to conventional heat treatment processes or conventional stabilization processes. In order to optimize overall recovery of T, $T_3$ and $T_3$-like products, the wet heat stabilization step is preferably carried out immediately following the dry heat stabilization step, in sequence, in the stabilization apparatus. However, depending on how the plant source is stored after dry heat stabilization, the wet heat stabilization can be postponed up to about one month. Optimal conditions for storage are those that do not permit regeneration of enzymes which have been inactivated in the dry heat stabilization step. Such conditions are those of low temperature and low moisture.

In the wet heat stabilization stage, moisture is introduced into the apparatus by means of water mixture, atomizing dispenser or condensing steam. As with the dry heat stabilization stage, wet heat stabilization is also carried out under a blanket of superheated steam, inert gas or vacuum. Superheated steam is preferred.

During wet heat stabilization, FFA build-up in plant material is more responsive to residence time in the stabilization apparatus than to temperature. Typically, the residence time of the plant material is between about 10 and about 500 seconds to minimize the occurrence of enzymatic activity before stabilization is completed. The preferred residence time is typically about 50 seconds, depending on pressure, temperature and moisture. These conditions insure the inactivation of any enzymes which remain active after the first dry heat stabilization stage and further aid in the release of Tocol products contained in the plant material.

Advantageously, collets are formed during the wet heat stabilization step. These serve to facilitate the extraction of oil and significantly reduce the fine-content of that oil. Fines cause product loss and removing them makes the separation steps more difficult. This second stabilization step thus minimizes the destruction of Tocol products and simplifies their recovery process. As in the dry heat stabilization step, microwaving the plant source before or after extrusion may aid in rupturing the cells of the plant source and minimizing enzymatic destruction of the Tocol products.

In the second stabilization stage, the parameters of temperature, pressure, treatment time and moisture, may be varied in concert from the ranges illustrated herein, while still providing a stabilized plant material. One of ordinary skill in the art can readily select a specific combination of treatment conditions, as long as those conditions are effective to inactivate Tocol-destroying enzymes, interfere with interactions which retain Tocol products in the plant material, or both. In addition, the treatment conditions should not lead to destruction of the desired Tocol products, decomposition of the non-Tocol containing by-products or unwanted side reactions, such as oxidizing pyrolysis and Maillard reactions.

After a one or two stage stabilization, the stabilized plant source is cooled. The source may be cooled within tubes using cold water and a cold water blanket or a refrigerant or compressed gas. Preferably, cooling is accomplished with cold water in the tubes of a cooler. The stabilized plant material is placed in the cooler and should be blanketed with an inert gas, such as $N_2$, to prevent an increase in peroxide value of the Tocol-containing products. The resulting product is a Tocol-rich stabilized, cooled, plant material. An example of one such product, as shown in FIG. 1, is a Tocol-rich stabilized, cooled rice bran.

After stabilization and cooling, further processing of the stabilized plant material is optional. Such processing is desirable when separating oil and Tocol products.

Figure 2:
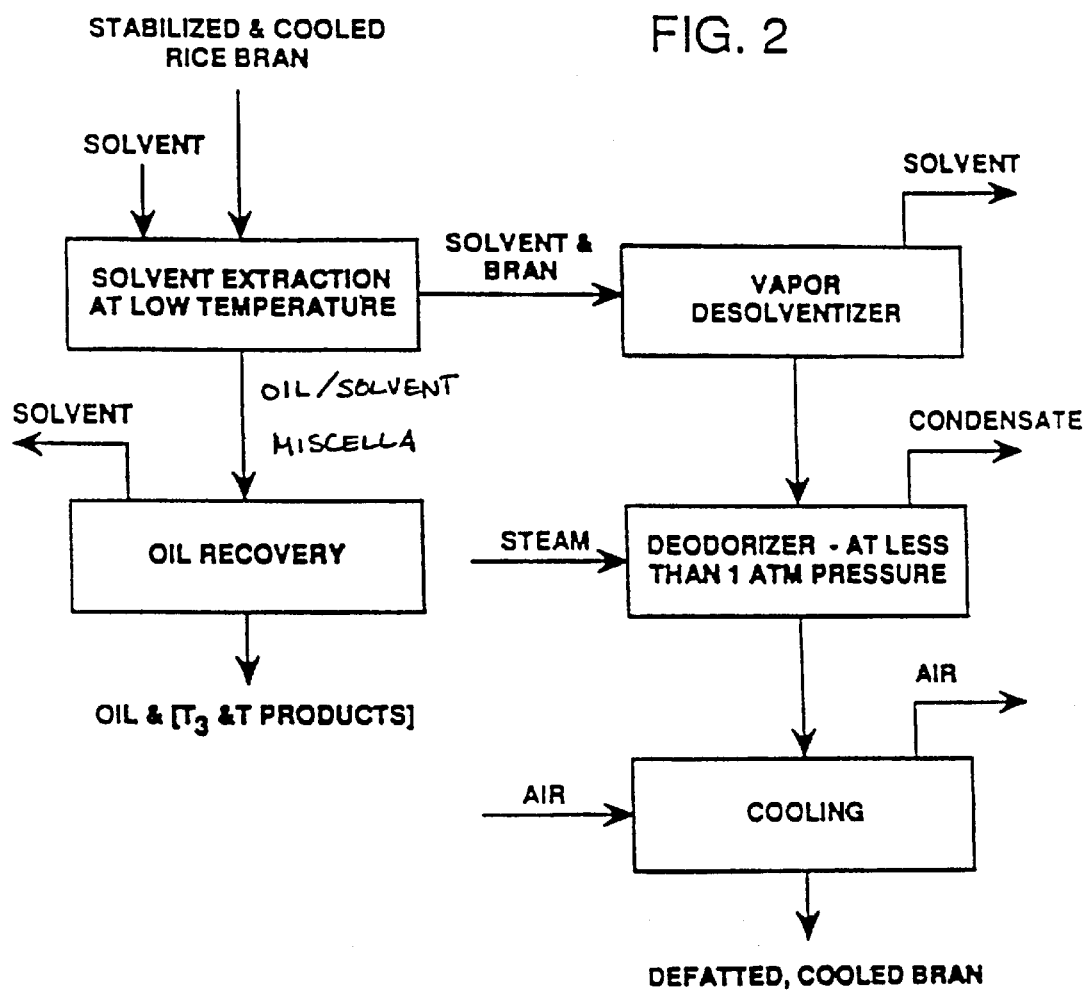
FIG. 2 is a schematic of one embodiment of the processes of the present invention for extracting Tocol-rich oil from a Tocol-containing grain or other biological source. The products of this process are a Tocol-rich oil and a defatted, cooled biological source in which lysine, cysteine, B vitamins and other temperature sensitive components thereof have been preserved.
Figure 3:
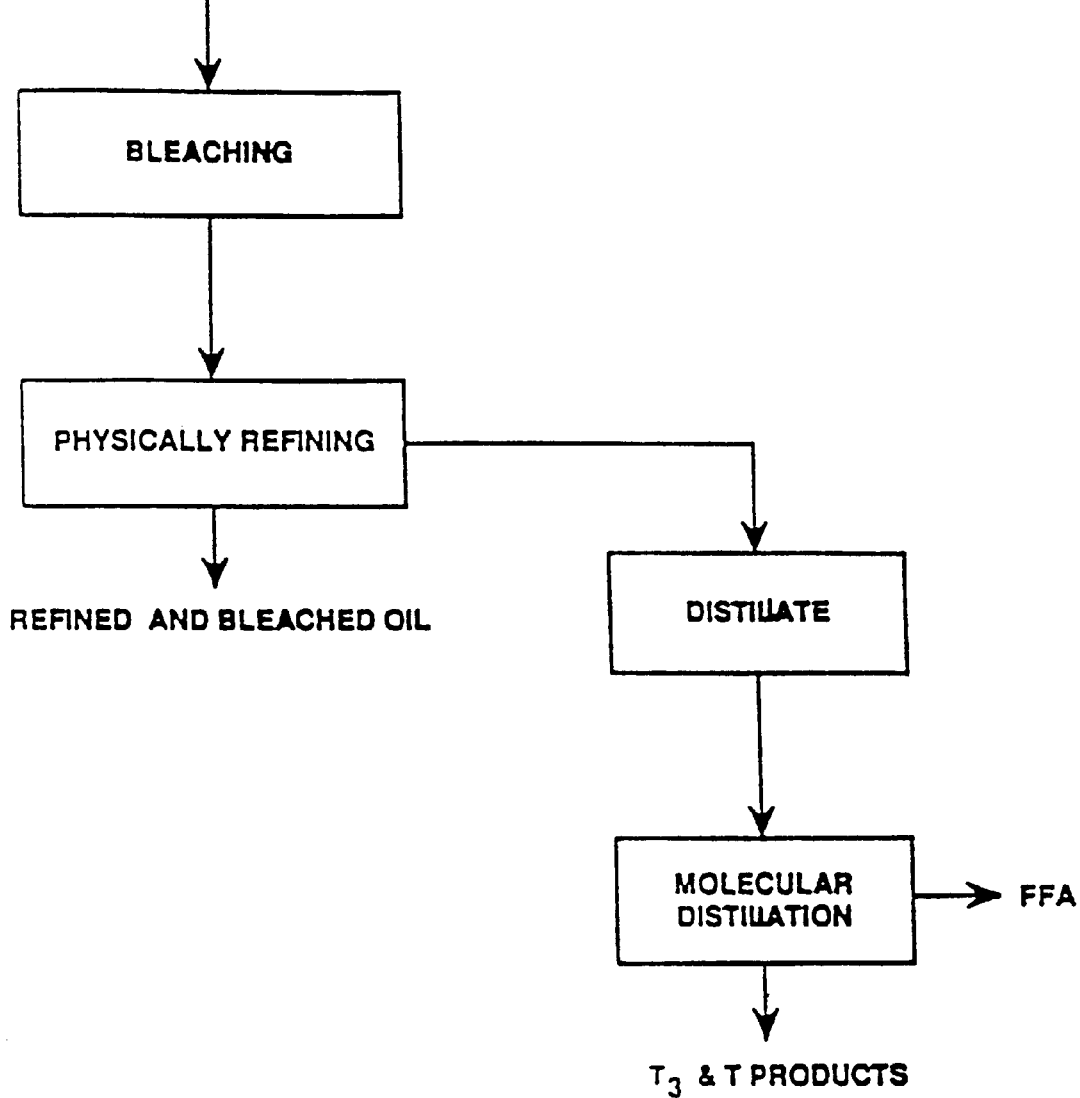
FIG. 3 is a schematic of one embodiment of the processes of the present invention for treating Tocol-rich oil and separating that oil into refined and bleached rice oil, Tocol-rich products and free fatty acids.
Figure 4:
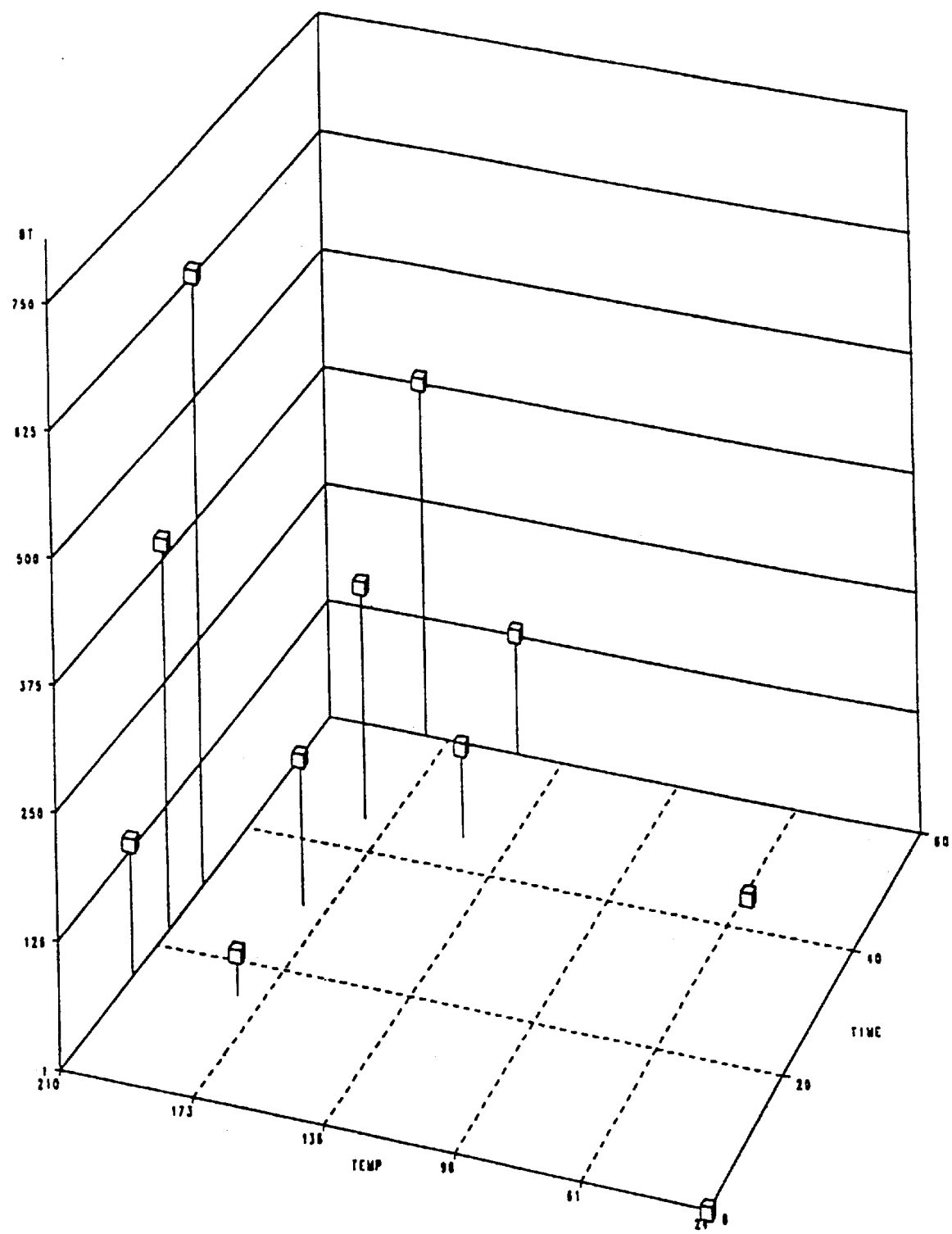
FIG. 4 is a plot of time, temperature and relative recoverable content (ppm) of P6 Tocotrienol from Basmati Bran.
Figure 5:
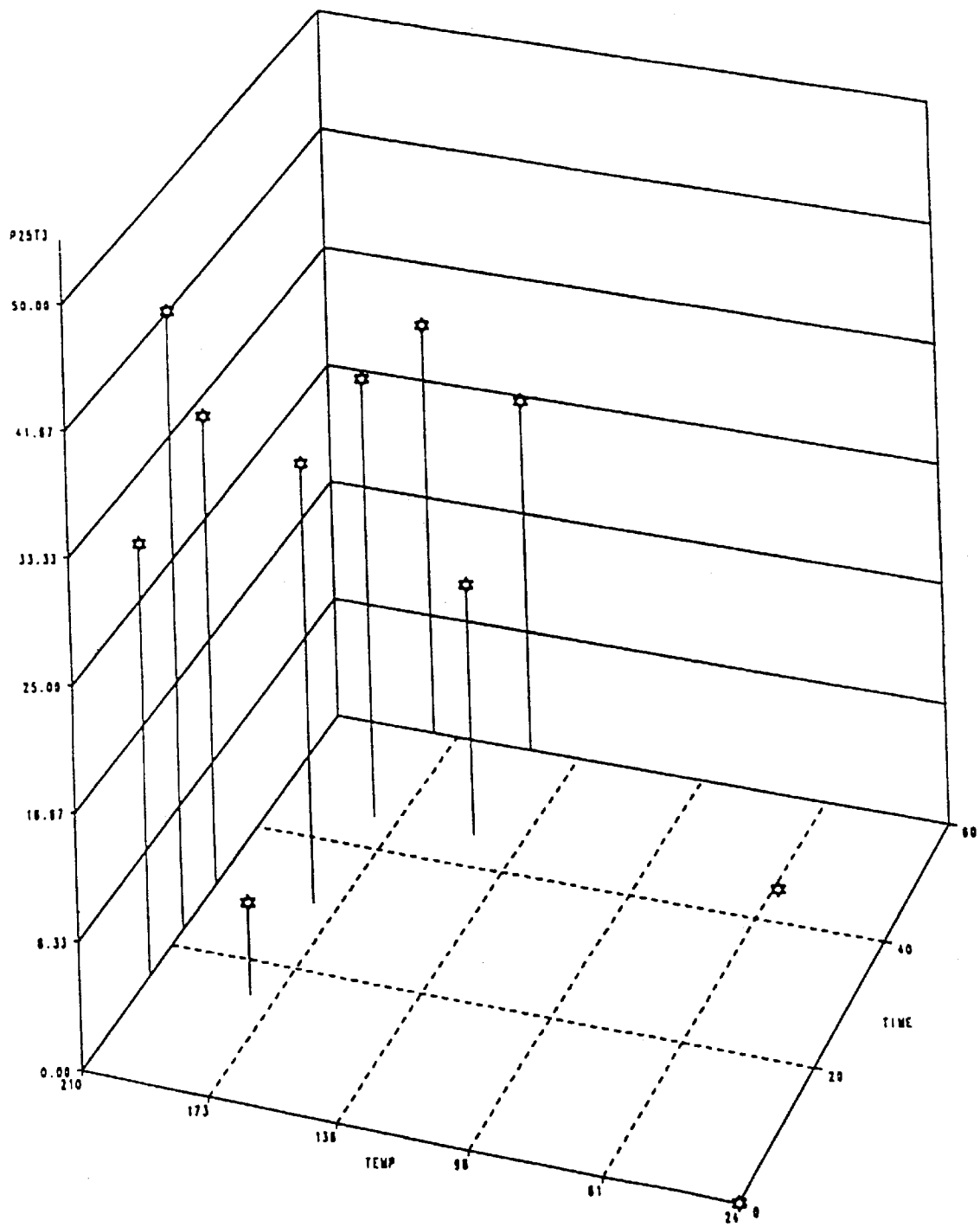
FIG. 5 is a plot of time, temperature and relative recoverable content (ppm) of P25 Tocotrienol from Basmati Bran.
Figure 6:
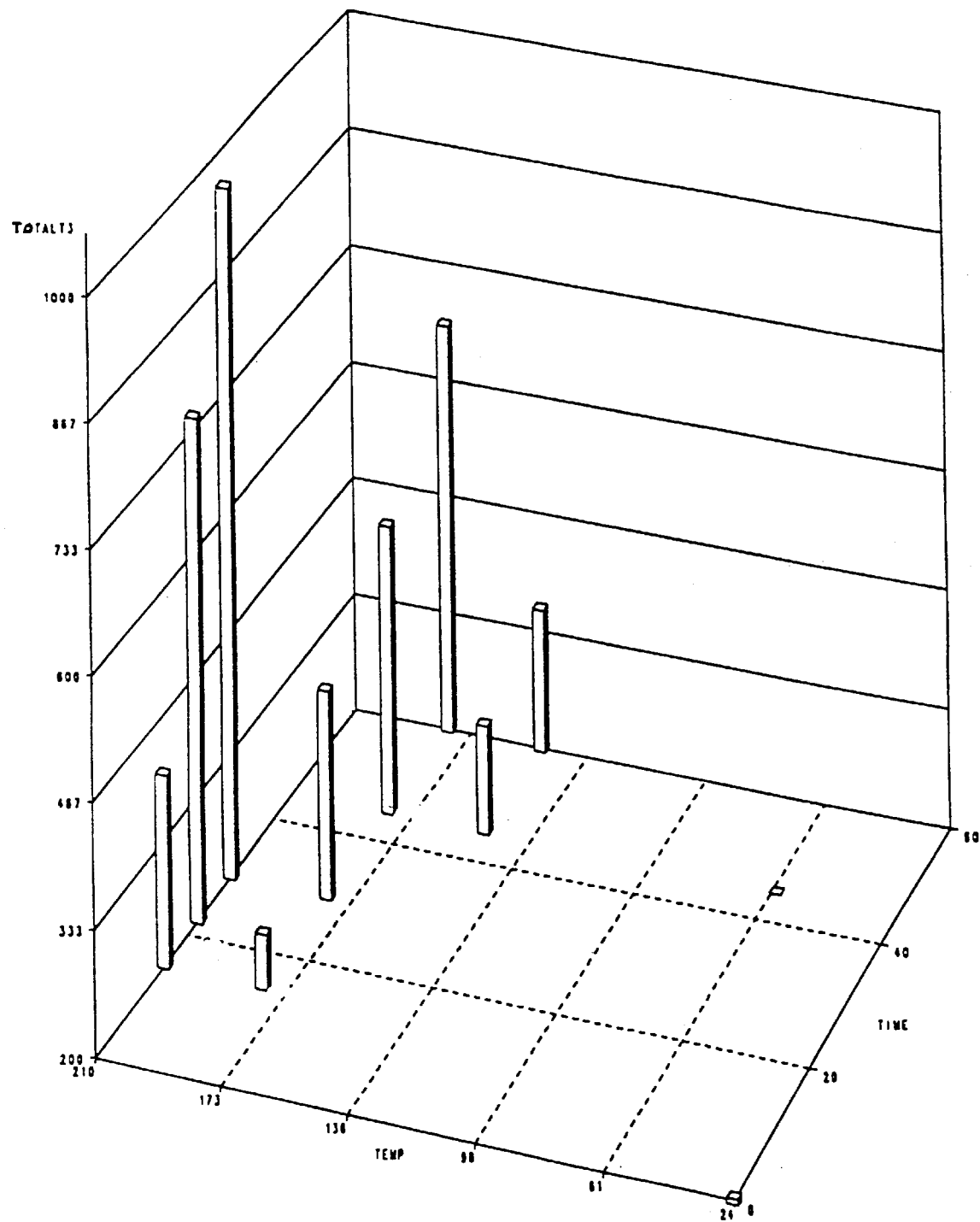
FIG. 6 is a plot of time, temperature and relative recoverable content (ppm) of Total Tocotrienols from Basmati Bran.
Figure 7:
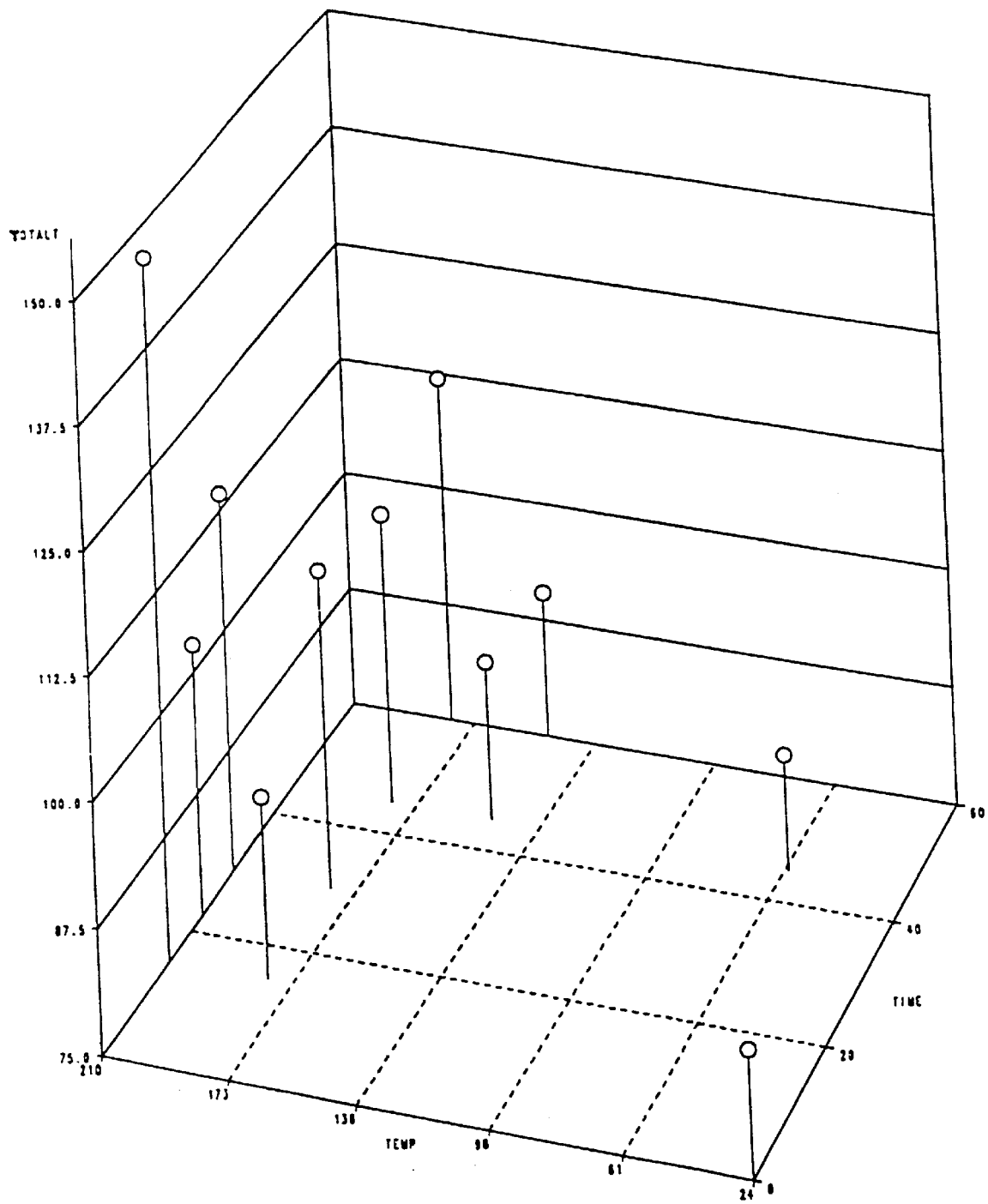
FIG. 7 is a plot of time, temperature and relative recoverable content (ppm) of Total Tocopherols from Basmati Bran.
Figure 8:
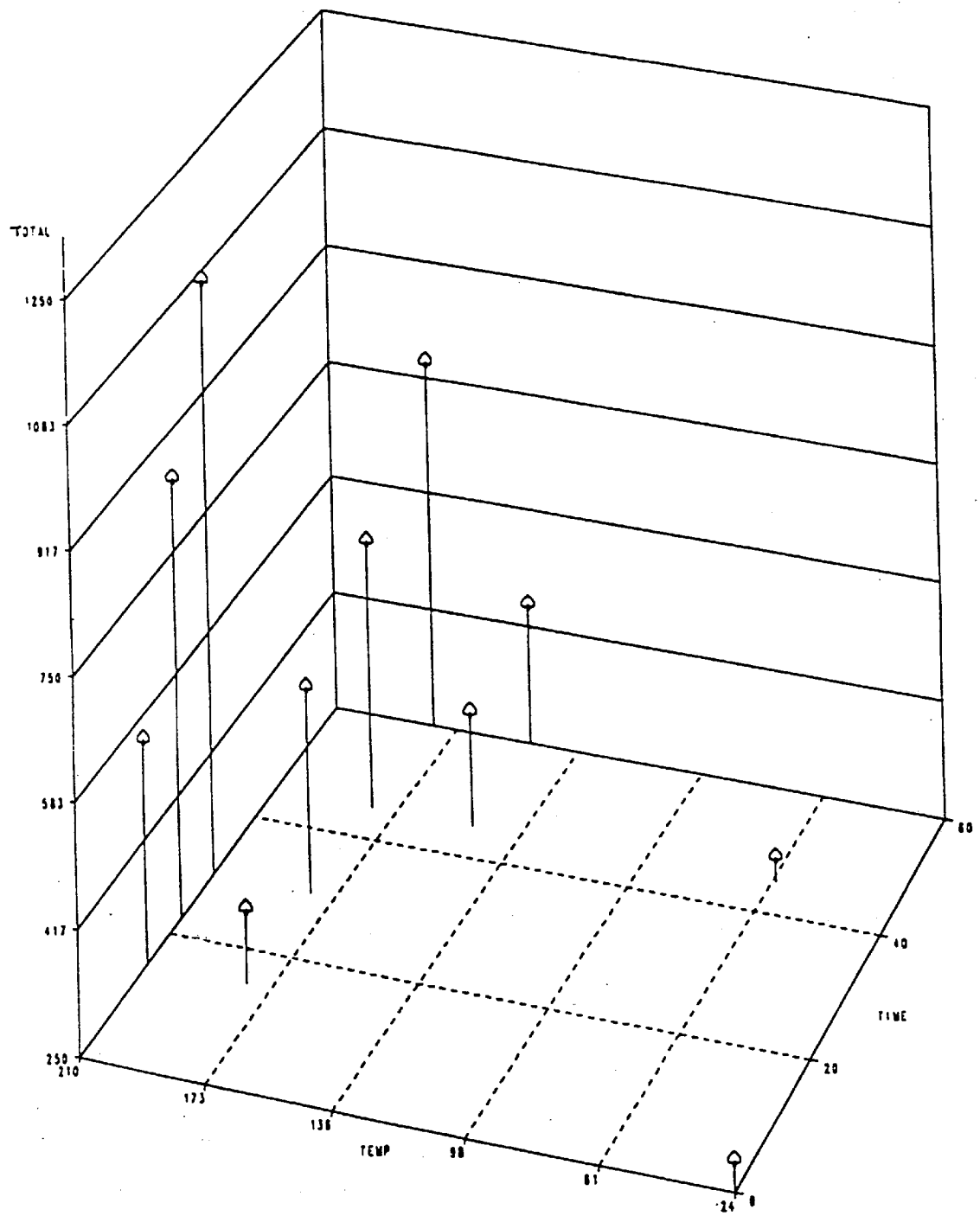
FIG. 8 is a plot of time, temperature and relative recoverable content (ppm) of Total Tocopherols plus Total Tocotrienols from Basmati Bran.
Figure 9:
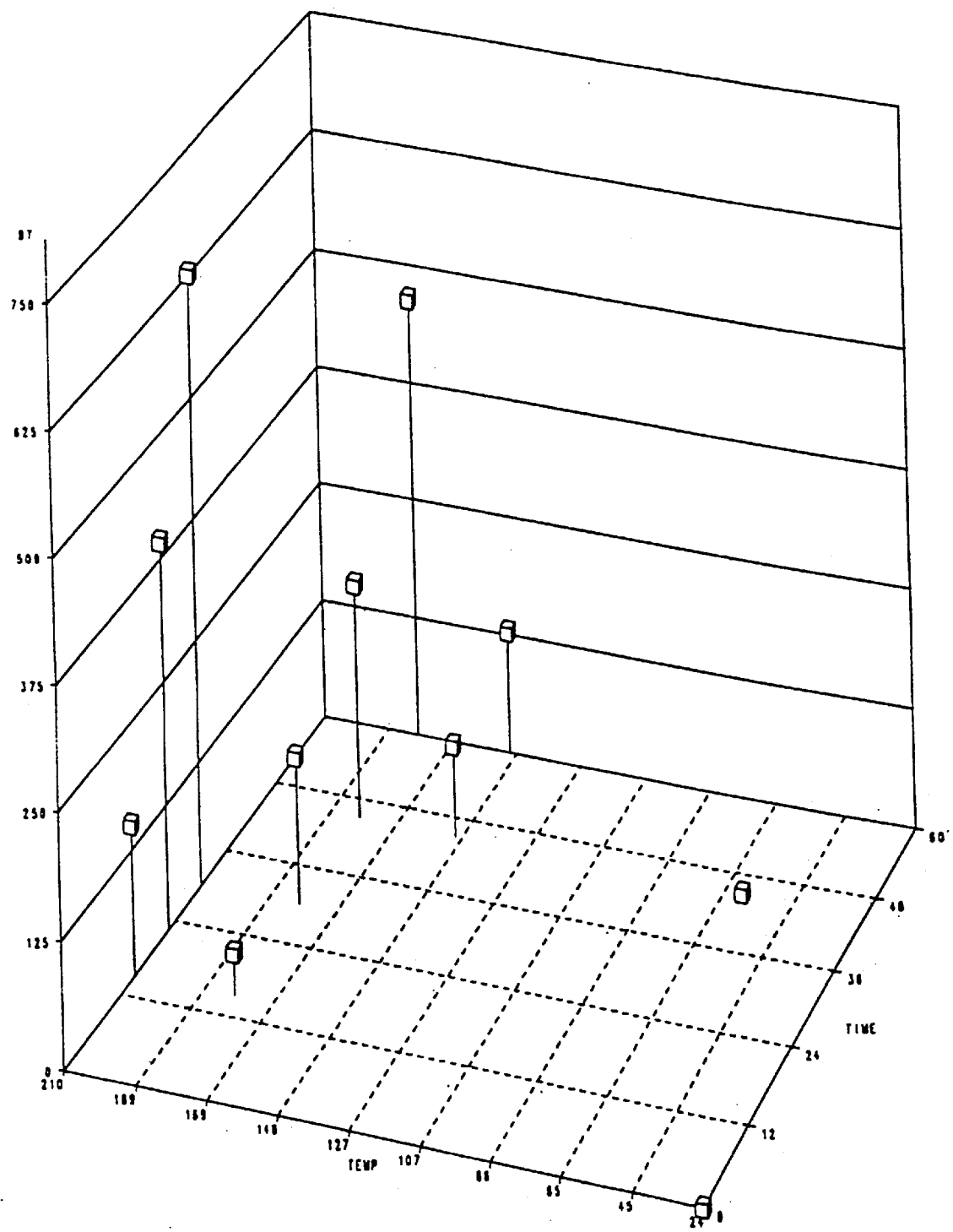
FIG. 9 is a plot of time, temperature, and recoverable content (ppm) of P6 Tocotrienol from a combined rice bran sample.
Figure 10:
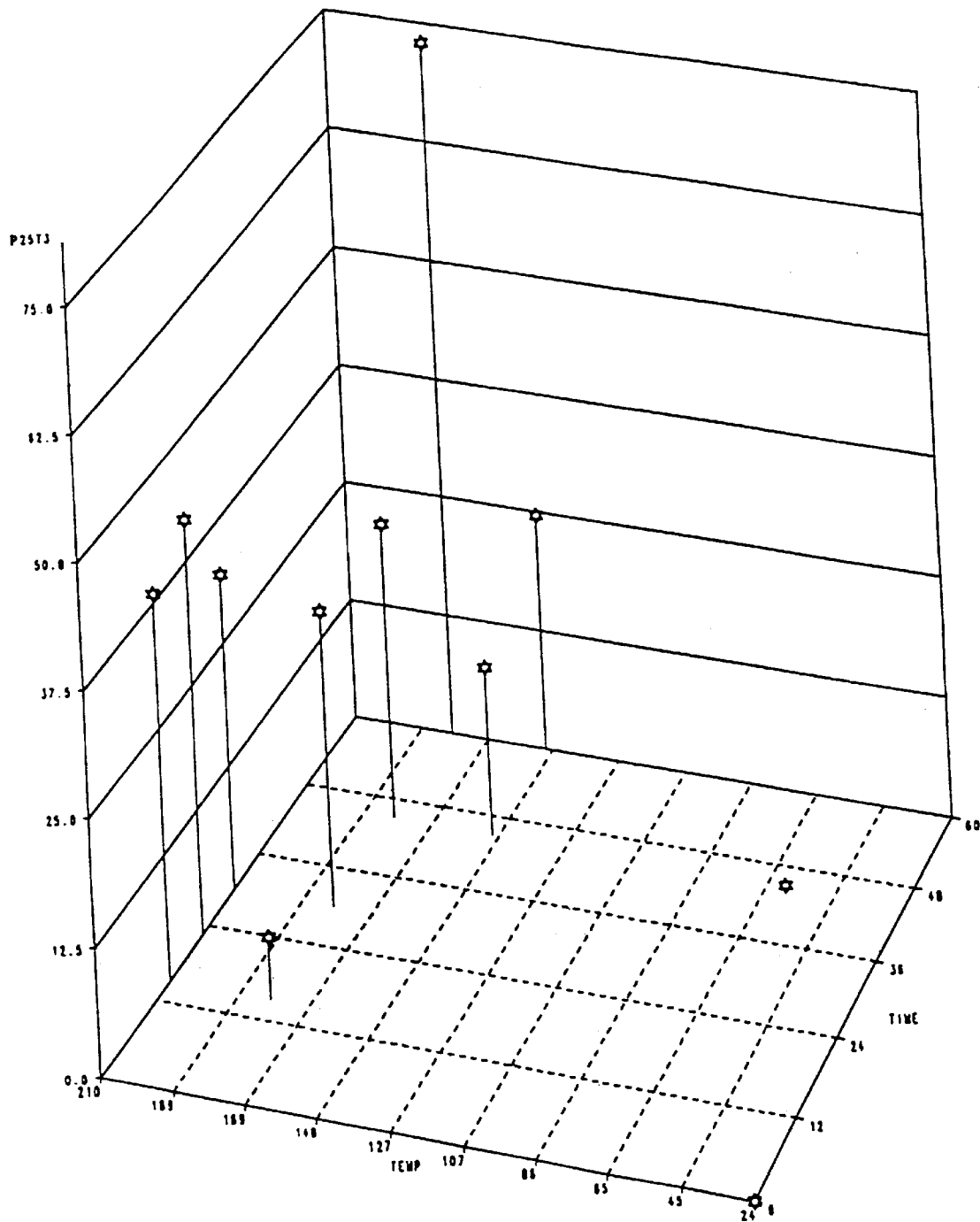
FIG. 10 is a plot of time, temperature, and recoverable content (ppm) of P25 Tocotrienol from a combined rice bran sample.
Figure 11:
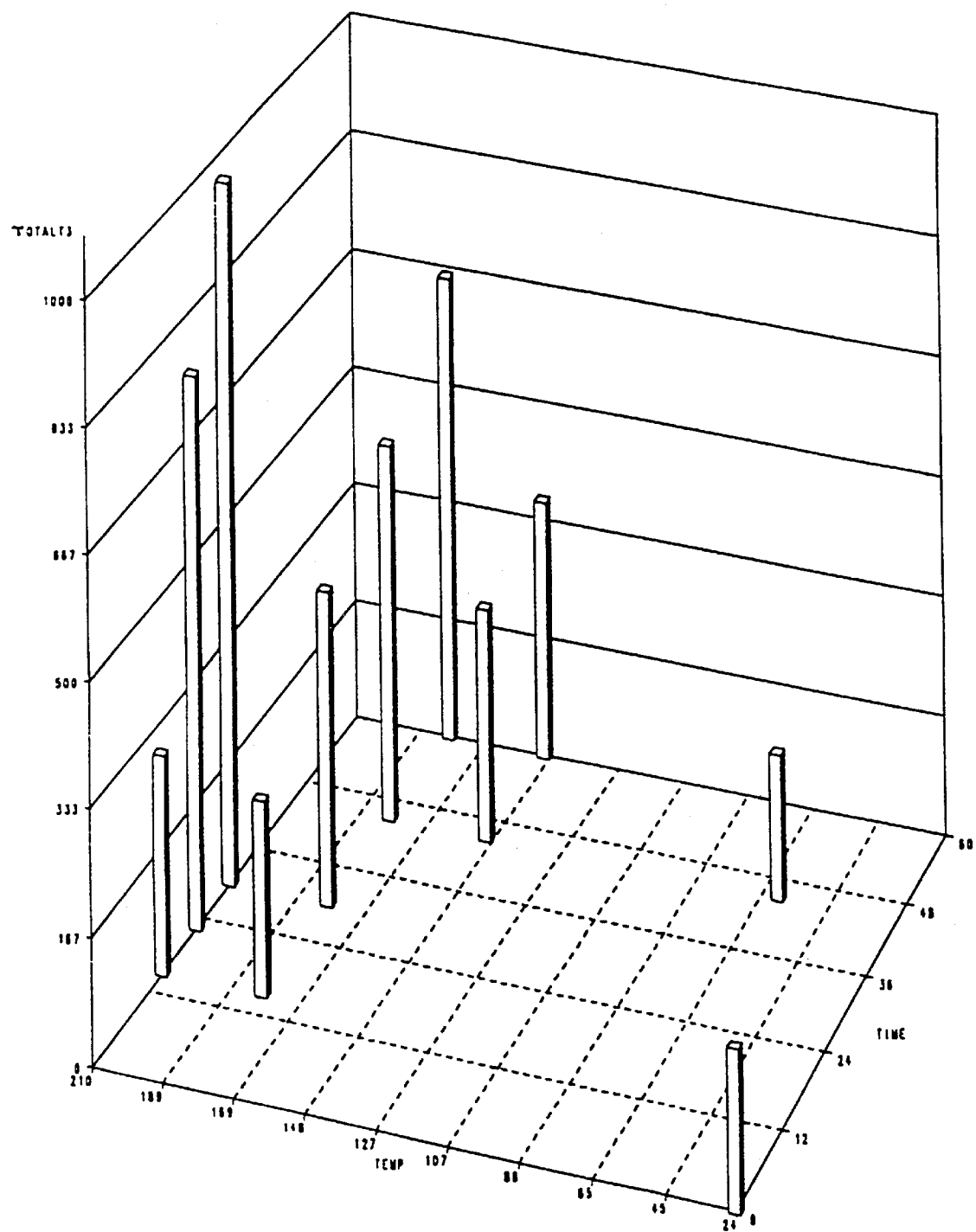
FIG. 11 is a plot of time, temperature, and recoverable content (ppm) of Total Tocotrienols from a combined rice bran sample.
Figure 12:
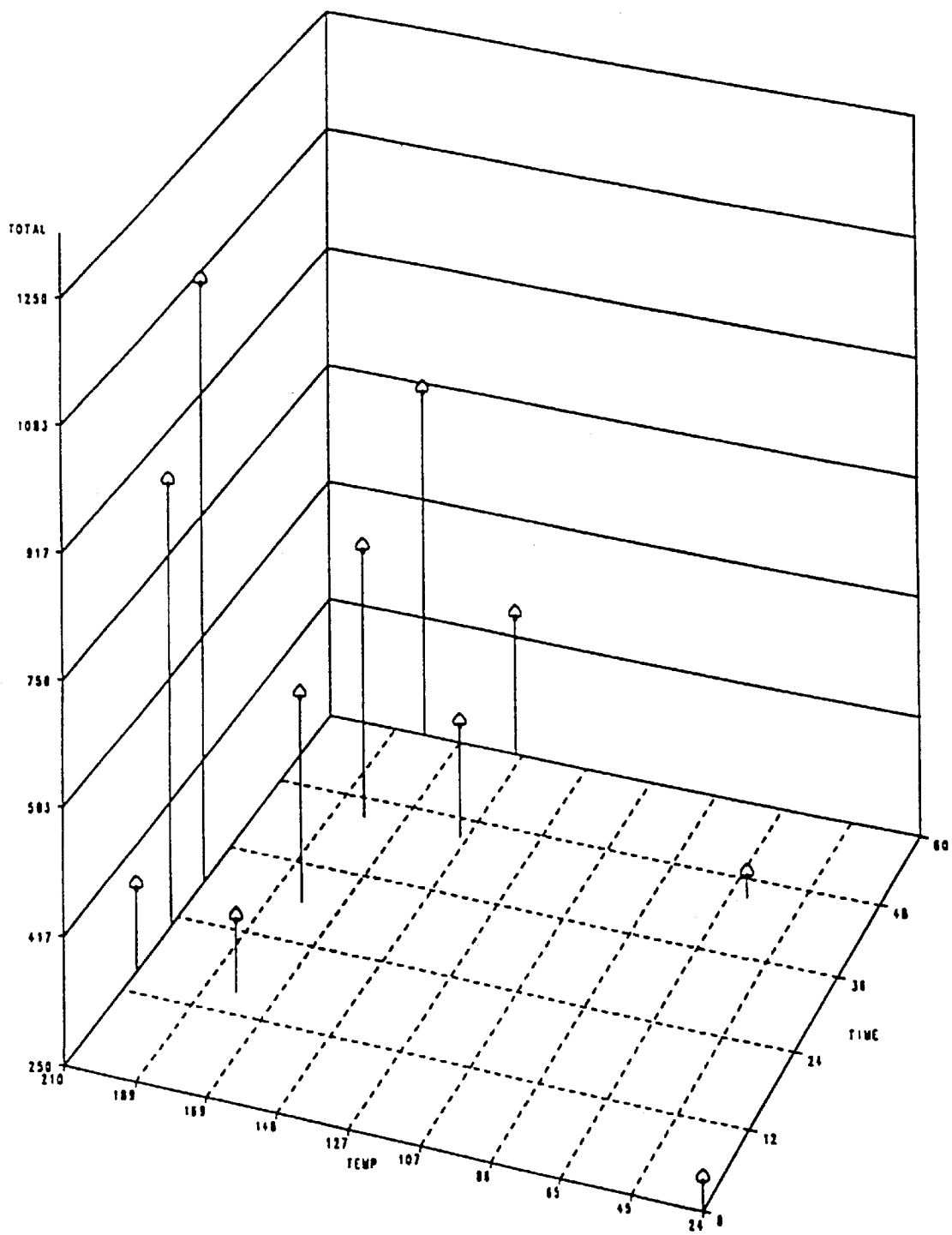
FIG. 12 is a plot of time, temperature, and recoverable content (ppm) of Total Tocopherols plus Total Tocotrienols from a combined rice bran sample.
Figure 13:
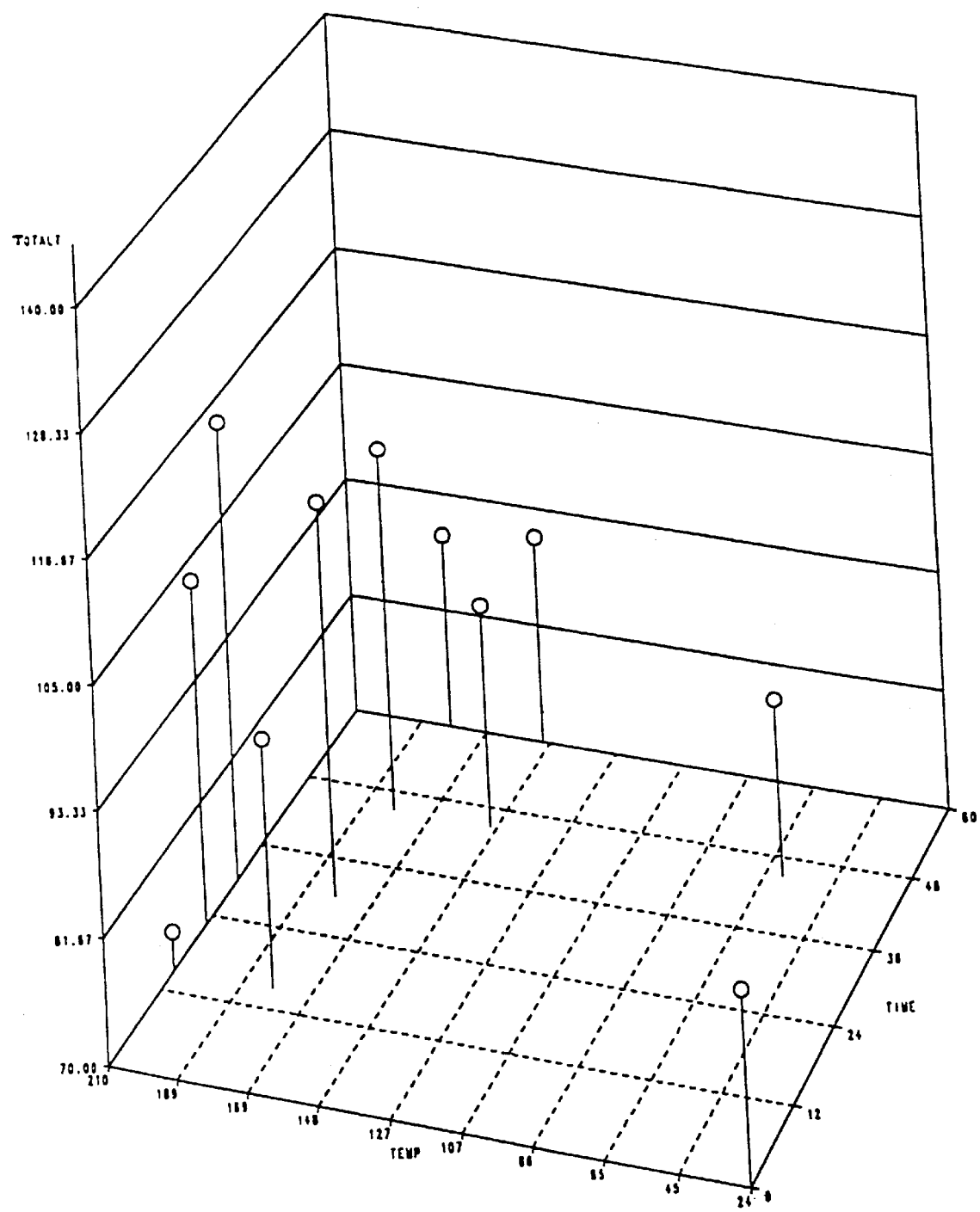
FIG. 13 is a plot of time, temperature, and recoverable content (ppm) of Total Tocopherols from a combined rice bran sample.
Figure 14:
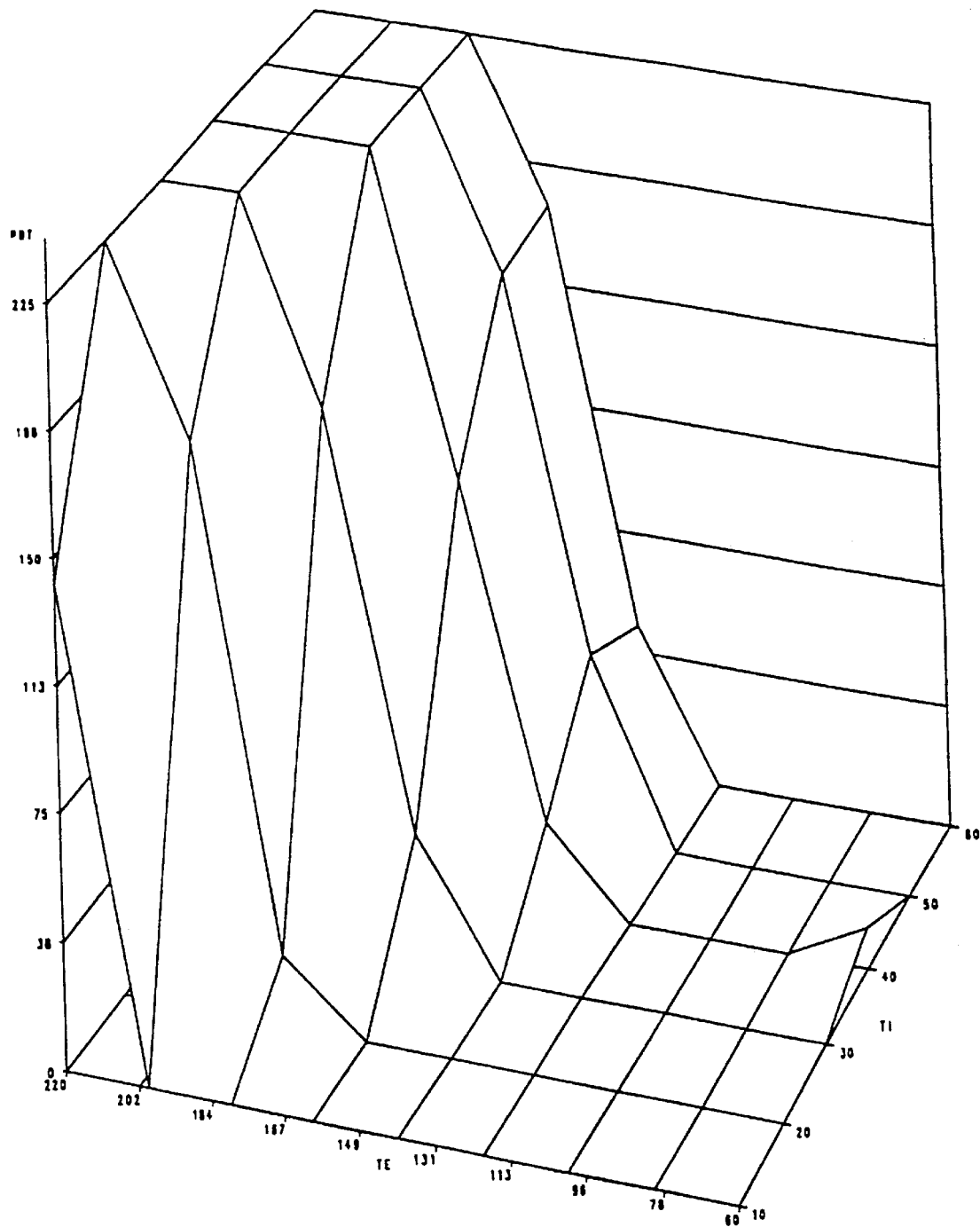
FIG. 14 is a response surface graph of time, temperature, and relative recoverable content (ppm) of P6 Tocotrienol from a combined rice bran sample, after quadratic model smoothing.
Figure 15:
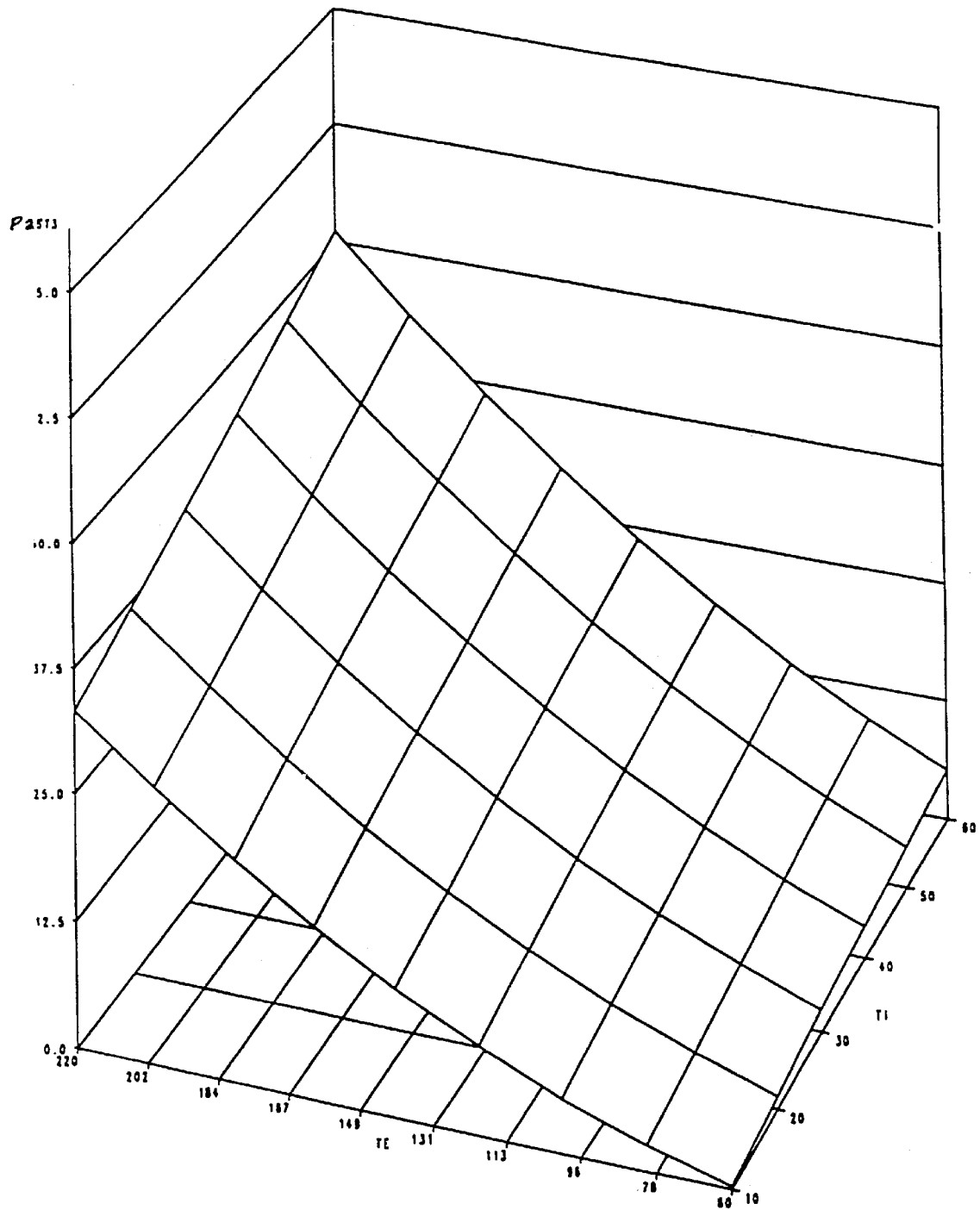
FIG. 15 is a response surface graph of time, temperature, and relative recoverable content (ppm) of P25 Tocotrienol from a combined rice bran sample, after quadratic model smoothing.
Figure 16:
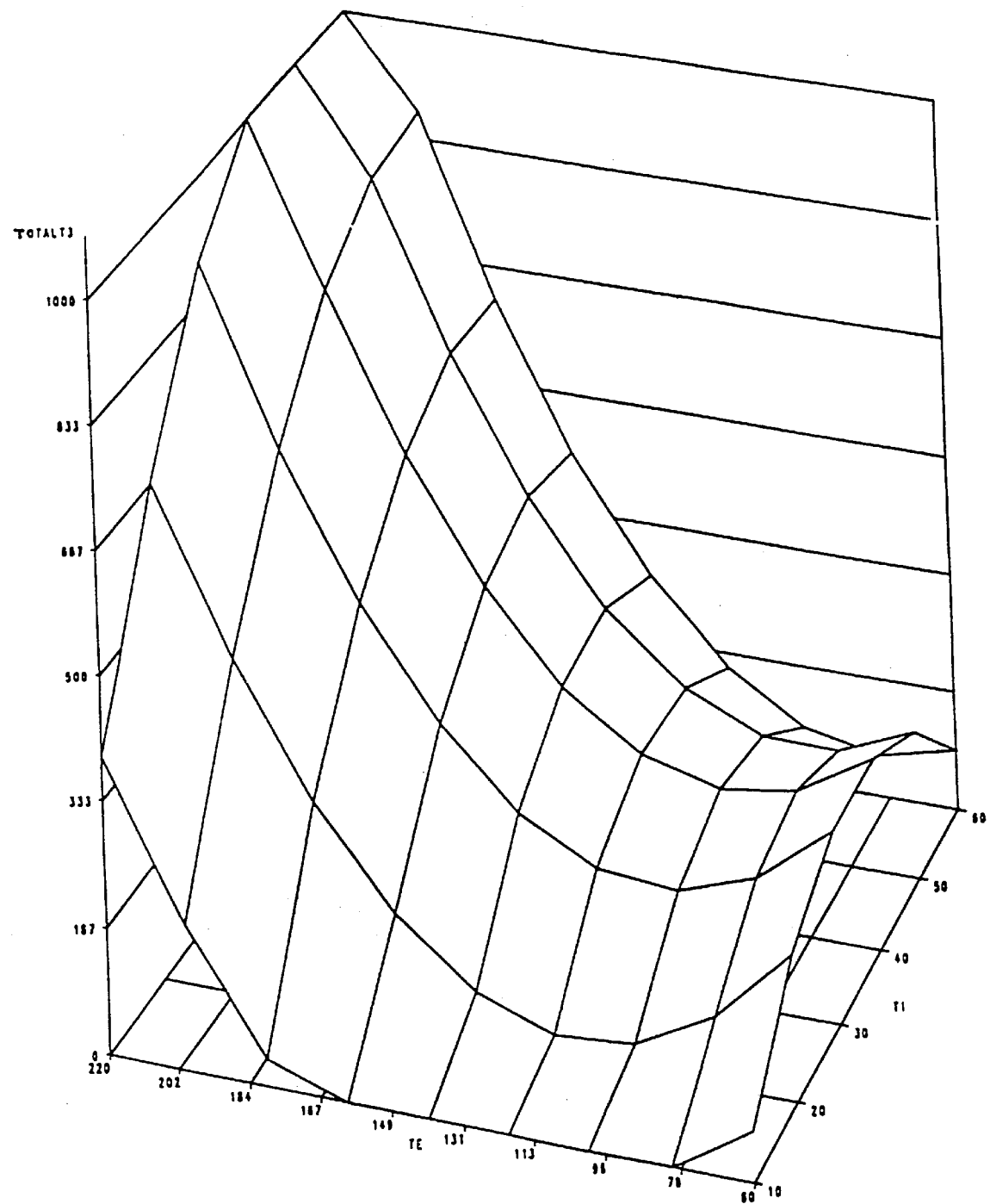
FIG. 16 is a response surface graph of time, temperature, and relative recoverable content (ppm) of Total Tocotrienols from a combined rice bran sample, after quadratic model smoothing.
Figure 17:
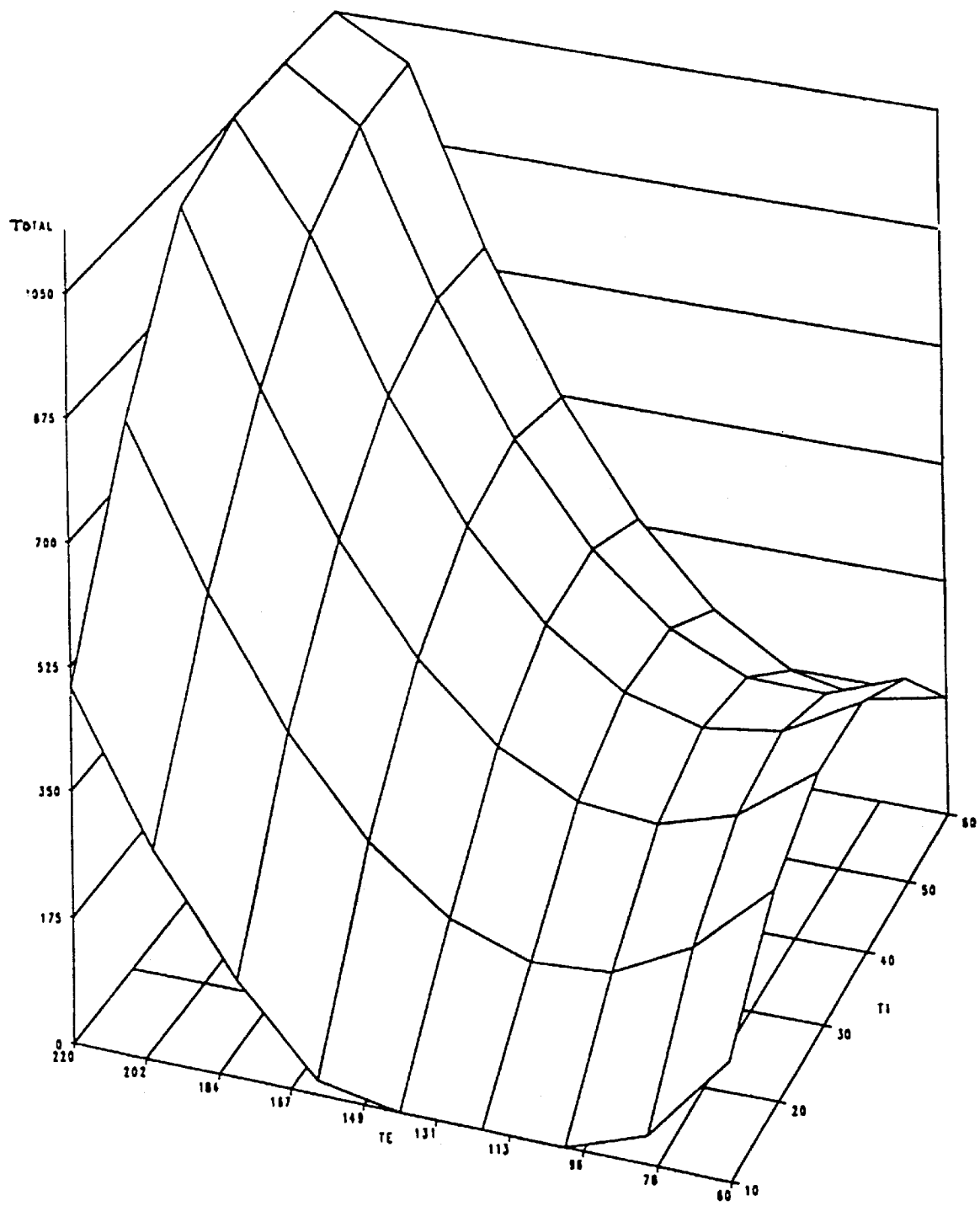
FIG. 17 is a response surface graph of time, temperature, and relative recoverable content (ppm) of Total Tocopherols plus Total Tocotrienols from a combined rice bran sample, after quadratic model smoothing.

As illustrated in FIG. 2, the Tocol products may be recovered from the Tocol-rich stabilized and cooled plant source at low temperatures, such as between about 5° C. and 45° C., depending on the specific solvent, using conventional techniques and equipment, such as commercial solvent extraction. Preferably, the extraction is carried out at temperatures at or below about 35° C., as opposed to the temperatures of 50° C. to 60° C. used in conventional hexane methods. At the low temperatures maintained to recover the Tocol products from the stabilized plant source according to this invention, the yield of T, $T_3$ and $T_3$-like compounds is maximized. For example, the yield of Tocol products at cold extraction (about 21° C.) is much higher than at hot extraction (60° C.). Under such conditions, the residual meal of a plant source retains waxes without retaining the desired $T_3$ products. Waxes are difficult to remove from the $T_3$ products because they are non-polar compounds and are very similar in structure to $T_3$. Extraction is preferably conducted in a continuous extraction unit with an organic solvent such as, for example, propane, pentane, butane, hexane, heptane, ethyl alcohol, diethyl ether, ether and ethanol acetate. Extraction may be carried out, for example, in a Rotocel.

For plant sources such as soybean, cottonseed, wheat germ, corn germ and rice bran, the preferred organic solvent is pentane. With pentane, the boiling point is about 35° C. and extraction can be carried out at about 25° C., without creating an explosive hazard. With hexane, however, the boiling point is about 60° C. and extraction cannot be carried out in a practical manner much below 50° C., without allowing air to enter the extractor and thereby creating the risk of explosion. For extractions conducted at temperatures below about 25° C., other solvents, such as propane, heptane or ethyl alcohol, for example, 95% ethyl alcohol, can also be used. Alternatively, pentane, hexane, heptane or ethyl alcohol, or mixtures thereof, may be used for extraction. The most preferred extraction solvent is a mixture of propane, butane and hexane. Advantageously, when this mixture of solvents is used, the stabilized extraction temperature may be lowered to about 5° C.

Alternatively, a hexane-operating system may be wrapped with pentane or butane. This allows the extraction to be carried out at low temperatures—down to 40° C. with pentane and down to 5° C. with butane.

In order to retain the Tocol products in the stabilized plant material, extraction is carried out at about 30° C. or less for between about 15 to about 40 minutes. To maximize recovery of Tocol products from a stabilized plant material, while retaining the maximum yield of Tocol products in the oil and a considerable quantity of waxes in the meal, extraction is carried out at about 5° C. to about 45° C. The extraction time will depend on the material bed formed during extraction. Extraction may also be carried out using supercritical conditions, such as supercritical carbon dioxide. Supercritical carbon dioxide extraction may be carried out under about 5 to about 15,000 PSI pressure at a temperature above about 31.6° C. for approximately 1 minute. Preferably, extraction may be carried out using supercritical carbon dioxide under about 10,000 to about 12,000 PSI pressure for about 1 minute, after which the pressure is released.

For certain plant sources, the commercial feasibility of recovering Tocol-rich products at low temperatures is increased if the extraction is preceded by cold pressing the stabilized plant source using a screw press under an inert gas blanket to reduce oil content from about 15–20% down to about 3.5–8.5%. Any remaining oil may then be extracted using cold ethanol, methanol, isopropanol or another organic solvent at a temperature below about 25° C.

The products of extraction of a stabilized plant source are a mixture of solvent and a Tocol-rich oil and an extracted plant source which preferably retains its nutritive value. The oil-solvent mixture is conventionally separated from the meal and solvent by a gravity drain. Then the solvent is evaporated and steam stripped. The recovered oil, depending on the temperature of extraction, contains a low concentration of FFA and waxes and a high concentration of Tocol products. Advantageously, maintenance of cold temperatures during extraction leads to retention of FFA and waxes in the meal, and a high concentration of Tocol products in the oil.

Any residual solvent is removed from the extracted plant source using a vapor desolventizer-deodorizer, a flash desolventizer-deodorizer, or an equivalent system, using recirculated superheated vapor in the desolventizer stage to remove more than 95% of the solvent from the extracted plant source. In the deodorizer stage, the system is typically operated in a pressure range of less than about 1 mm to 6 mm Hg. Preferably, the pressure is below about 1 atmosphere in order to remove solvent down to an acceptable level. Preferably, less than 600 ppm solvent remains in the extracted plant source after the desolventization stage. This assures minimum destruction of valuable products, such as lysine, cysteine, and B-vitamins contained in the meal.

The desolventized plant source is further cooled by conventional means, for example, by contacting it with air or by cooling with water in the tubes of the cooler. The desolventized extracted meal may be used as an edible source of lysine, cysteine, B-vitamins and other essential nutrients. An inert gas, such as nitrogen, can be employed to maintain the mixture of solvents and gases in the apparatus below the explosive limit and also to help remove solvent from the meal. Sparge steam may also be introduced to aid in the removal of solvent. Typically, the sparge steam is introduced counter current to the meal in order to remove the solvent to an acceptable level.

The recovered Tocol-rich oil may also be processed further. For example, the oil may be degummed. Degumming may be carried out, for example, by washing the oil with water, thereby dissolving the gummy substances in the water layer. And the oil may be bleached to remove colored bodies. Bleaching techniques involve heating the refined oil together with an adsorbent powder, such as natural, or acid-activated bleaching earths, preferably with activated clay (clay to which non-compressible clay has been added as a filtering aid). As a result of bleaching, colored materials are physically adsorbed onto activated clay, which is then filtered. Preferably, this step is carried out under vacuum to avoid oxidation of the oil and to improve bleaching efficiency.

The bleached Tocol-rich oil may then be subjected to physical refining techniques, reduced-pressure molecular distillation (preferably in the range of about 5 $\mu$M Hg to about 6 mm Hg), or both, to provide a distillate containing only the Tocol products and FFA. Physical refinement techniques include low pressure, high temperature vacuum distillation. During physical refinement, sparge steam is preferably used to remove the Tocol products and FFA from the oil. When physical refining is employed, molecular distillation is used to separate the FFA from the Tocol fraction.

Alternatively, either ethanol or methanol may be used to achieve phase separation with the oil. The alcohol can then be distilled off, thereby separating the FFA and Tocol products. Molecular distillation is preferred for recovering the Tocol products.

The tocopherol-rich fraction, tocotrienol-rich fraction and tocotrienol-like compound-rich fractions may be separated from the Tocol-rich products by any conventional technique used to separate chemical structures, such as supercritical extraction. A preferred technique comprises passing the Tocol mixture through a silica gel column. Advantageously, the $T_3$ or $T_3$-like products are retained on the silica gel, while the T products pass through and are collected. The $T_3$ or $T_3$-like compounds may then be recovered by washing the silica gel with an organic solvent such as diethyl ether, pentane, hexane, heptane, ethanol, methanol, or combinations thereof. The solvent is then evaporated using conventional means to yield purified $T_3$ or $T_3$-like compounds.

In addition to a process for recovering Tocol-rich oil from stabilized biological sources, this invention also provides a process which yields a defatted, Tocol-rich stabilized biological source, preferably a plant source. For example, a polar medium, such as supercritical $CO_2$, may advantageously be used to remove the oil products from a stabilized plant source while retaining most of the Tocol products in the meal. The operating conditions (i.e., temperature and pressure) can be adjusted to maximize the amount of Tocol retained in the defatted meal. This process may also be used to extract $T_3$ or $T_3$-like compounds from Tocol-rich oil and to break down components of the $T_3$ fraction or $T_3$-like compound fraction.

In a particularly preferred embodiment, a biological source is stabilized by heat treatment in an extruder under 180–220° C. at the die or casting part of the extruder. The product is extracted with alcohol, particularly isopropyl alcohol and/or hexane. An optional preferred embodiment is to perform a low temperature extrusion followed by solvent extraction, and then a high temperature extrusion followed by solvent extraction. The low temperature extrusion occurs at 50–200° C., more preferably 100–200° C., while the high temperature extrusion occurs at 200–500° C., or 200° C. and above. During this process, the bran, which starts out at a white color, is darkened to a color which resembles dark chocolate.

The Tocol-rich products obtained by the processes of this invention are useful in pharmaceutical compositions and food formulations. As used herein, the term "food formulation" refers to any food additive, dietary supplement, foodstuff, or edible composition suitable for consumption by humans and animals. Advantageously, these products are hypocholesterolemic and hypolipidaemic agents.

Pharmaceutical compositions may take the form of tablets, capsules, emulsions, suspensions and powders for oral administration, sterile solutions or emulsions for parenteral administration and sterile solutions for intravenous administration. The pharmaceutical compositions may be administered to humans and animals in a safe and pharmaceutically effective amount to substantially lower the blood level of LDL-cholesterol and total serum cholesterol. Hypercholesterolemic-related diseases which may be treated using such compositions include, but are not limited to, arteriosclerosis, atherosclerosis, xanthomatosis, hyperlipoproteinemias, and familial hypercholesterolemia.

These compositions may also be used to treat hypertension and to increase the production of insulin in Type 2 diabetic patients. In addition, these compositions are useful for prophylactic treatment of those patients having multiple risk factors for hypercholesterolemia who are as yet asymptomatic.

The pharmaceutical compositions of this invention typically comprise a pharmaceutically effective amount of a Tocol-rich product of this invention and a pharmaceutically acceptable carrier. Therapeutic and prophylactic methods of this invention comprise the step of treating patients in a pharmaceutically acceptable manner with those compositions. As used herein, the term "pharmaceutically effective amount" or "cholesterol-lowering effective amount" refers to an amount effective to lower blood levels of LDL-cholesterol and total serum cholesterol, while increasing the ratio of HDL-cholesterol to LDL-cholesterol in the blood. Alternatively, the term "pharmaceutically effective amount" refers to an amount effective to prevent blood levels of LDL-cholesterol and total serum cholesterol associated with hypercholesterolemia, an amount effective to increase production of insulin in Type 2 diabetic patents or an amount effective to prevent or decrease hypertension.

The pharmaceutical compositions of this invention may be employed in a conventional manner for the treatment and prevention of hypercholesterolemia. Such methods of treatment and prophylaxis and their dosage levels and requirements are well-recognized in the art and may be chosen by those of ordinary skill in the art from available methods and techniques. The dosage and treatment regimens will depend upon factors such as the patient's health status, the severity and course of the patient's hypercholesterolemia or disposition thereto and the judgment of the treating physician.

The Tocol-rich products of this invention may also be used in combination with conventional therapeutics used in the treatment or prophylaxis of hypercholesterolemia. Such combination therapies advantageously utilize lower dosages of those conventional therapeutics, thus avoiding possible toxicity incurred when those agents are used as monotherapies.

In food formulations, the Tocol-rich products of this invention may be used in amounts and combined with any biologically acceptable carrier to provide a safe and effective means of substantially lowering blood levels of LDL-cholesterol and total serum cholesterol while increasing the ratio of HDL-cholesterol to LDL-cholesterol. In addition, such food formulations may be used to increase production of insulin in Type 2 diabetics or to prevent or decrease hypertension. The Tocol-rich products of this invention may be combined with any foodstuff to produce such food formulations. Tocol-rich oils obtained by the processes of this invention may be sprayed on foodstuffs, such as cereals. And Tocol-rich oils may be used as a cooking oil or a salad oil. Tocol-rich grains may be used in foodstuffs, such as baked goods, cereals, pastas and soups.

The pharmaceutical compositions and food formulations of this invention may be administered to humans and animals such as, for example, livestock and poultry. Advantageously, livestock and poultry raised on such foodstuffs may, in turn, constitute foodstuffs useful in the treatment or prophylaxis of hypercholesterolemia.

In order that this invention be more fully understood, the following examples are set forth. These examples are for purposes of illustration only, and are not to be construed as limiting the scope of the invention in any way.

In each example in which the FFA content was determined, it was so done using the official AOCS method Ca Sa-40. The T and $T_3$ concentrations, recorded in ppm, were determined using the HPLC methods described in V.

Piironen et al., "High Performance Liquid Chromatographic Determination Of Tocopherols And Tocotrienols And Its Application To Diets And Plasma Of Finnish Men," *Internat. J. Vit. Nutr. Res.*, 53, pp. 35–40 (1984) and B. Tan et al., "Separation Of Tocopherol And Tocotrienol Isomers Using Normal- And Reverse-Phase Liquid Chromatography," *Anal. Biochem.*, 180, pp. 368–373 (1989).

EXAMPLE 1

Raw bran from freshly milled rice was collected in polybag-lined fiber drums and held for 24 hours at ambient temperature (32° C.). After 24 hours, the free fatty acid content of the bran had risen to 2.4% or 11.0% on an oil basis (the oil comprised 22% w/w of the bran).

At 12–13% moisture, approximately 2,700 lbs. of the bran was fed into the #1 extruder head of a Wenger X-25 single screw extruder at a rate of 15 lbs./min. An operating pressure of 300–400 PSI and a discharge temperature of 162° C. were maintained. The retention time of the extruder was approximately 30 seconds.

The bran was then ground to a fine powder (approximately 200 mesh). Hexane was added and extraction was performed at room temperature (24° C.) for 20 minutes. The hexane/oil mixture was decanted and then the hexane was evaporated under aspiration vacuum. The residual oil was then analyzed by HPLC.

The result of HPLC Tocol analysis is displayed in Table 1.

EXAMPLE 2

Pre-stabilization and stabilization conditions were as described in Example 1, except that the stabilization apparatus was an Anderson 8 inch single screw expander with a 5/16"×1" die. At 12–13% moisture, approximately 540 lbs. of the bran was fed into the extruder at a rate of 3.2 lbs./min. No steam or water injection was carried out. The screw rpm was 125, resulting in a discharge temperature of 96° C. The retention time was approximately 50 seconds.

Extraction was performed using the procedure detailed in Example 1.

The result of HPLC Tocol analysis is displayed in Table 1.

EXAMPLE 3

Pre-stabilization and stabilization conditions were as described in Example 2, except that the stabilization apparatus was fitted with a ¼"×1" die to improve collet shape and the bran treated was a sample of approximately 360 lbs. In addition, steam was injected at the fourth bolt hole at a rate of 12 lbs./hr. The screw rpm was 275, resulting in a discharge temperature of 107° C. The retention time was approximately 30 seconds.

Extraction was performed using the procedure detailed in Example 1.

The result of HPLC Tocol analysis is displayed in Table 1.

EXAMPLE 4

Pre-stabilization conditions and sample treated were as described in Example 1, except that the sample size was 2 lbs. No stabilization was carried out.

Extraction was performed using the procedure detailed in Example 1.

The result of HPLC Tocol analysis is displayed in Table 1.

EXAMPLE 5

Pre-stabilization conditions were as described in Example 1, except that the sample size was approximately 1800 lbs.

Stabilization was initiated within 5 minutes of bran removal in a Wenger X-25 extruder with a 5/16"×1" die. The jacketing barrel was cooled with water to 121° C. No steam or water injection was carried out. The operating pressure was 800 PSI. The retention time was about 30 seconds.

Extraction was performed with hexane at 60° C. until the residual oil weighed less than 1% of the total weight of the bran. The hexane/oil mixture was decanted. Then, the bran was washed with hexane and the combined hexane extracts were evaporated under aspirator vacuum. The residual oil was washed with water to degum and was then analyzed by HPLC.

The FFA content was approximately 4% on an oil basis. The FFA content rose over time.

The result of HPLC Tocol analysis is displayed in Table 1.

EXAMPLE 6

Pre-stabilization and stabilization conditions and the stabilization apparatus were the same as in Example 5.

In this example, however, the jacketing barrel was not cooled, resulting in a stabilization temperature of 160° C. The retention time was about 30 seconds.

Extraction was performed using the procedure detailed in Example 5, except that the temperature was lowered to 21° C.

The FFA content was approximately 4% on an oil basis. The FFA content did not rise over a two month period.

The result of HPLC Tocol analysis is displayed in Table 1. As shown in that table, rice bran stabilized according to this invention produced an oil containing 4179 ppm of Tocol products ($T_3$=2394 ppm and T=1785 ppm). In contrast, unstabilized rice bran produced an oil containing in the range of 25 ppm Tocol products (see Example 4).

EXAMPLE 7

Pre-stabilization conditions and stabilization apparatus were the same as in Example 5.

Stabilization conditions were the same as Example 6, except that after 6 weeks, the bran was further wet stabilized in the same apparatus using 20% moisture at 113° C.

Extraction was performed using the procedure detailed in Example 5.

The FFA content was approximately 4% on an oil basis.

The result of HPLC Tocol analysis is displayed in Table 1.

EXAMPLE 8

The wax fraction obtained by dewaxing crude rice bran was analyzed by HPLC to determine the amount of Tocol products remaining after the degumming and physical refinement steps.

The result of HPLC Tocol analysis is displayed in Table 1.

TABLE 1

| Example No. | [T + T$_3$] in oil ppm |
|---|---|
| 1 | 331 |
| 2 | 74 |
| 3 | 73 |
| 4 | 26 |
| 5 | 2512 |
| 6 | 4179 |
| 7 | 2497 |
| 8 | 338 (T only) |

As demonstrated in Table 1:

the ppm of T and T$_3$ products in the oil was optimized when stabilization was carried out immediately after milling;

a high temperature dry stabilization stage was far superior to a low temperature dry stabilization stage;

stabilized bran yielded a higher degree of T and T$_3$ products in the recovered oil than unstabilized bran;

a delay of 6 weeks between the dry and wet stage stabilizations allowed enzymatic activity of the slower acting enzymes, such as the peroxidases to decrease T and T$_3$ content in the oil.

EXAMPLE 9

The following is a typical protocol for carrying out this invention, using rice bran as the sample biological source.

Rough rice (paddy rice) from a farm is dried in a commercial-type continuous flow, non-mixing, heated air dryer. Drying is carried out to lower the moisture content of the rice a level of between about 18 and 22 percent to a level between about 10 and 13 percent. The dried rice is then cleaned by removing dust, stones, seeds and sticks by aspiration in a commercial rice cleaning machine, followed by gravity separation in a stoner and particle size separation in a disk grader and a drum separator. The husks are then removed using a rubber roller sheller. Paddy (husks or hulls) were removed using a paddy separator for the first pass, followed by a paddy separator for the second and third passes. The bran is then removed in a friction mill to yield polished rice. The raw bran is then pneumatically conveyed to the extruder or for storage until stabilization.

When stabilization is desired, the raw bran is pneumatically conveyed to a filter/sifter to remove residual broken rice. After sifting, the raw bran is pneumatically conveyed to a mixing/tempering hopper tank. The raw bran is conveyed from the discharge of the mixing tank to the extruder inlet valve of a clamped barrel single screw) extruder by a metered screw conveyer feeder. The operating conditions of the extruder are maintained during stabilization in the following range:

flow rate: 900–2000 lbs./hr.
pressure: 800–2000 PSI
temperature: 135–180° C.
time: 15–90 seconds.

The dry heat stabilized bran is then fed directly into the feed hopper of an expander cooker. Alternatively, the feed to the cooker may be raw bran that has been cooled with dry ice. Within that extruder, the bran is conveyed by a discontinuous worm shaft toward the discharge plate at a rate of around 341 lbs./hr. Water and steam are added through injection ports in the barrel of the extruder at a rate of around 38 lbs./hr. to completely mix the material and to raise the moisture level. The ambient temperature is about −3° C. Flow of the material is controlled by a discharge die plate at a rate of about 341 lbs./hr. The moisture level is maintained at about 114 lbs./hr. and the temperature is held between about 90° and 135° C. for between about 15 and 90 seconds.

As the bran is extruded through the die plate, the sudden decrease in pressure causes the liquid water to vaporize. During cooking, enzymes are denatured and some constituents of the bran are gelatinized into a fluid paste which binds the particles together. A compact pellet is formed. Vaporization of water caused breakage within the cells ideally suited for solvent migration percolation. The introduction of steam and water during the process raises the moisture content of the bran to about 22–25 percent. The extruder discharge is then sent downstream at a rate of around 341 lbs./hr. to a dryer/cooler. Moisture flow was maintained at about 96 lbs./hr. and the temperature is kept in the range of 82° C. to 130° C. The discharge from the dryer/cooler is maintained at a rate of about 341 lbs./hr. and at a moisture level of about 30 lbs./hr. These conditions allow for storage of the stabilized bran.

The stabilized bran is immersed in hexane in a ratio by weight of about two to one. Typically, about 10–100 g of material can be extracted using this protocol. The hexane is generally heated to about 60° C. using a steam table incorporated into an explosion proof vented hood, but other solvents and other temperatures may also be employed. The hexane/oil miscella is removed from the bran by filtration. About 5–6 washings are necessary to bring the oil content of the bran to less than one percent. The defatted bran and the hexane/oil miscella are both desolventized under gentle heating with steam.

If 100–500 lbs. of stabilized bran is to be extracted, it is more practical to use the following protocol. The stabilized bran is fed into a counter-current extractor at a flow rate of about 111 lbs./hour. Fresh hexane is introduced at a rate of around 312 lbs./hr. The fresh solvent temperature is maintained at about 50° C., while the extractor temperature is maintained at around 52° C. The residence time in the extractor is typically around 45 minutes. The product is a defatted bran with an oil content of less than one percent. The hexane/oil miscella exiting the discharge of the extractor is filtered through a plate and frame filter press. The filtered miscella is then pumped to a steam heated still where the hexane is evaporated and collected by a condenser for reuse.

Following extraction and desolventization, crude rice bran oil is typically degummed, dewaxed, bleached and physically refined using steam distillation. Degumming is carried out by a two stage addition under agitation of 2% water by weight and then 0.15% phosphoric acid (85% reagent grade) by weight. The temperature is held at about 82° C. to 88° C. for 10 minutes. Then the sludge containing the gums is removed via ultrafugation. (See U.S. Pat. No. 4,049,686). The degummed bran is cooled to about 5° C. to 8° C. and held for 24 hours. The dewaxed oils form a layer above the waxes which can be decanted using a vacuum pump. Bleaching is carried out according to the official AOCS method 6c 8a-52. Physical refining is carried out in a glass deodorizer at about 250° C. and around 3 mm Hg for about 2 hours.

While we have described a number of embodiments of this invention, it is apparent that our basic constructions may be altered to provide other embodiments which utilize the processes and products of this invention. Therefore, it will be appreciated that the scope of this invention is to be defined by the appended claims, rather than by the specific embodiments which have been presented by way of example.

EXAMPLE 10

The following is a description of the protocol used to determine the time and temperature dependency for Tocol product recovery from rice bran, as determined by chromatographic peak analysis. Samples of rice bran were wrapped in foil packages and labeled. The wrapped samples were then cooked at fixed pressure in a conventional oven, varying the time and/or temperature for each sample. Following heat exposure, samples were dissolved in methanol, the supernatant was removed, the solvent evaporated, and the residue was dissolved in hexane as a solvent for HPLC. Analysis by HPLC provided a chromatogram showing peaks which correspond to compounds eluted. The peaks were integrated by standard procedures to yield data on the temperature and time dependency for Tocol recovery. Two measurements at each time-temperature combination were used to determine the reproducibility of the method. The resulting data are shown in Table 2, reproduced below, which includes data sorted by bran and which indicates the increase in peak value as the time and temperature increased to 60 minutes and 180° C.

SCB Stabilized Cypress Bran (stabilized by treatment at 145° C. for 15 seconds)
XB Basmati Bran, all of which are commercially available (Riviana Foods, Abbyville, Louisiana).
The target compounds of interest are as follows:
BT P6 Tocotrienol (peak at ~6 minutes on HPLC)
$P25T_3$ P25 Tocotrienol
TOTAL T Total Tocopherols
TOTAL $T_3$ Total Tocotrienols
TOTAL Total Tocopherols plus Total Tocotrienols.

Five different rice bran samples shown in Table 2 were used to determine the relationship between peak value and time and temperature as a measure of the relative extractability of target compounds of interest. An analysis by rice bran sample indicated the same type of relationship for each sample. Graphs of time, temperature, and relative recoverable content (ppm) of compounds of interest for Basmati Bran are included in FIGS. 4–13 in order to obtain a perspective for the relationship of each peak to the time and temperature values.

Since the relationship for each rice bran sample exhibited the same pattern, all 5 rice bran samples were combined to

TABLE 2

DATA SUBDIVISION BY SAMPLE TYPE SHOWING RELATIVE EXTRACTABILITY (PPM) OF TARGET COMPOUNDS OF INTEREST AT VARYING TIMES AND TEMPERATURES FOR VARIOUS TYPES OF BRAN

| SAMPLE | TEMP | TIME | BT | $P25T_3$ | TOTAL T | TOTAL $T_3$ | TOTAL |
|---|---|---|---|---|---|---|---|
| BB-5 | 24 | 0.0 | 0.74 | 0.00 | 87.36 | 205.71 | 293.07 |
| BB-10 | 60 | 45.0 | 0.97 | 0.00 | 87.08 | 199.98 | 287.06 |
| BB-15A | 150 | 45.0 | 94.98 | 17.22 | 91.56 | 320.29 | 411.84 |
| BB-15B | 150 | 60.0 | 128.34 | 24.60 | 90.44 | 360.62 | 451.06 |
| BB-20C | 180 | 45.0 | 243.37 | 30.40 | 105.45 | 521.75 | 627.20 |
| BB-20B | 180 | 30.0 | 150.50 | 29.87 | 107.91 | 428.04 | 535.95 |
| BB-20A | 180 | 15.0 | 43.06 | 6.08 | 93.29 | 258.72 | 352.02 |
| BB-25 | 180 | 60.0 | 377.44 | 28.90 | 111.87 | 664.25 | 776.12 |
| BB-30 | 210 | 22.5 | 393.09 | 41.72 | 102.77 | 749.37 | 852.14 |
| BB-30C | 210 | 30.0 | 626.64 | 31.95 | 114.20 | 959.67 | 1073.87 |
| BB-30A | 210 | 15.0 | 133.04 | 28.75 | 146.56 | 406.79 | 553.35 |
| NB-2 | 24 | 0 | 0.20 | 0.00 | 89.05 | 204.73 | 293.78 |
| NB-7 | 60 | 45 | 0.76 | 0.00 | 88.99 | 193.24 | 282.23 |
| NB-12 | 150 | 45 | 108.56 | 24.49 | 106.35 | 360.92 | 467.28 |
| NB-17 | 180 | 45 | 202.34 | 29.26 | 107.01 | 467.06 | 574.07 |
| NB-22 | 180 | 60 | 287.29 | 30.33 | 111.60 | 578.36 | 689.96 |
| NB-27 | 210 | 15 | 64.63 | 13.72 | 97.82 | 285.01 | 382.83 |
| OB-1 | 24 | 0 | 0.00 | 0.33 | 91.44 | 205.93 | 297.37 |
| OB-6 | 60 | 45 | 1.91 | 0.00 | 94.26 | 183.67 | 277.93 |
| OB-11 | 150 | 45 | 118.80 | 18.78 | 116.02 | 348.56 | 464.58 |
| OB-16 | 180 | 45 | 172.56 | 34.51 | 98.40 | 410.69 | 509.09 |
| OB-21 | 180 | 60 | 214.83 | 28.19 | 115.61 | 458.82 | 574.43 |
| OB-26 | 210 | 15 | 102.05 | 18.32 | 92.67 | 328.17 | 420.84 |
| RCB-4 | 24 | 9 | 0.66 | 0.00 | 109.75 | 291.30 | 401.05 |
| RCB-9 | 60 | 45 | 1.29 | 0.00 | 109.05 | 276.41 | 385.46 |
| RCB-14 | 150 | 45 | 130.05 | 31.16 | 112.19 | 426.81 | 539.00 |
| RCB-19 | 180 | 45 | 279.50 | 35.53 | 126.42 | 640.25 | 766.66 |
| RCB-24 | 180 | 60 | 408.68 | 27.74 | 120.50 | 708.83 | 829.34 |
| RCB-29 | 210 | 15 | 142.38 | 59.32 | 122.78 | 529.93 | 652.71 |
| SCB-3 | 24 | 0 | 11.95 | 2.08 | 110.15 | 295.48 | 405.63 |
| SCB-8 | 60 | 45 | 10.62 | 1.88 | 110.02 | 325.90 | 435.92 |
| SCB-13 | 150 | 45 | 116.89 | 29.36 | 115.98 | 479.64 | 595.62 |
| SCB-18 | 180 | 45 | 259.69 | 36.87 | 113.98 | 600.10 | 714.08 |
| SCB-23 | 180 | 60 | 372.59 | 29.33 | 124.56 | 730.38 | 854.95 |
| SCB-28 | 210 | 15 | 145.87 | 36.02 | 118.43 | 479.16 | 597.59 |
| XB-31 | 180 | 60 | 464.72 | 72.88 | 89.15 | 654.35 | 743.49 |
| XB-32 | 210 | 15 | 150.00 | 38.45 | 73.63 | 292.47 | 366.10 |

The bran samples which appear above are as follows:
BB Basmati Bran type of cultivar bran
NB New Lamont Bran
OB Old Lamont Bran
RCB Raw Cypress Bran examine this relationship. This effectively increased the sample size which strengthened the significance of the relationship. Although using 5 different rice bran samples would increase the within bran variation, the overall pattern is better defined.

Graphs for the combined sample data set forth in Table 2 are generated using the computer program SAS 6.07 which is commercially available and known to those skilled in the art. A 3-dimensional graph of relative recoverable content for each compound of interest as a function of time and temperature for the combined sample is given in FIGS. 9–13. These graphs clearly indicate the increase in peak value as time and temperature increases. Response surface graphs of time, temperature, and relative removable content (ppm) of compounds of interest for the combined sample are graphed in FIGS. 14–17. The results have undergone quadratic model smoothing before being plotted in these figures.

The data from the study set forth above are analyzed to determine a strong relationship between time and temperature for 4 peaks. These 4 peaks which are characterized by their elusion times are b-T (5.84), p-25 $T_3$ (19.54), Total $T_3$, and Total (T+$T_3$). The percent variation explained in the peak variation measured as the correlation squared ×100 as given for each of these peaks using a quadratic model in time and temperature are as follows:

| Peak | Time - Temperature - Model |
| --- | --- |
| b$T_3$ | 82.5% |
| P-25 $T_3$ | 68.5% |
| Total $T_3$ | 77.0% |
| Total (T + $T_3$) | 75.8% |

As a general rule, 50% of the variation explained (correlation=0.7) is regarded as a good relationship. Above 75% is considered very good. The data indicate that there is a very strong evidence of significant increase in peak value as a function of increased time and temperature as the temperature is increased from 24° C. to 180° C., and the time is increased from initial time to 60 minutes.

EXAMPLE 11

Figure 18:
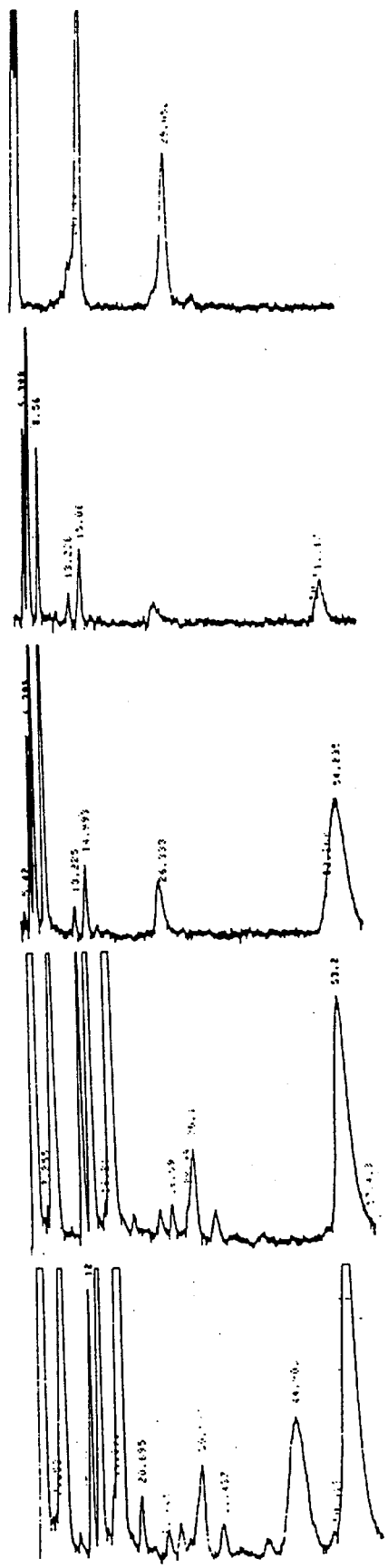
FIG. 18 shows HPLC chromatograms for Oat Bran unstabilized (TRF-Control), and stabilized for 1 hour at 24° C., 110° C., 150° C., and 180° C.

A sample comprising Oat Bran was heated in a vacuum oven for 1 hour at 24° C., 110° C., 150° C., and 180° C. Palm oil was used as a TRF-control. The product was extracted in at least one of methanol and hexane. The extraction utilized about 8 cc hexane per gram of stabilized biological material. The solvent was evaporated, and the remaining oil was redissolved in hexane for HPLC analysis. The resulting HPLC chromatograms are shown at FIG. 18.

Figure 19:
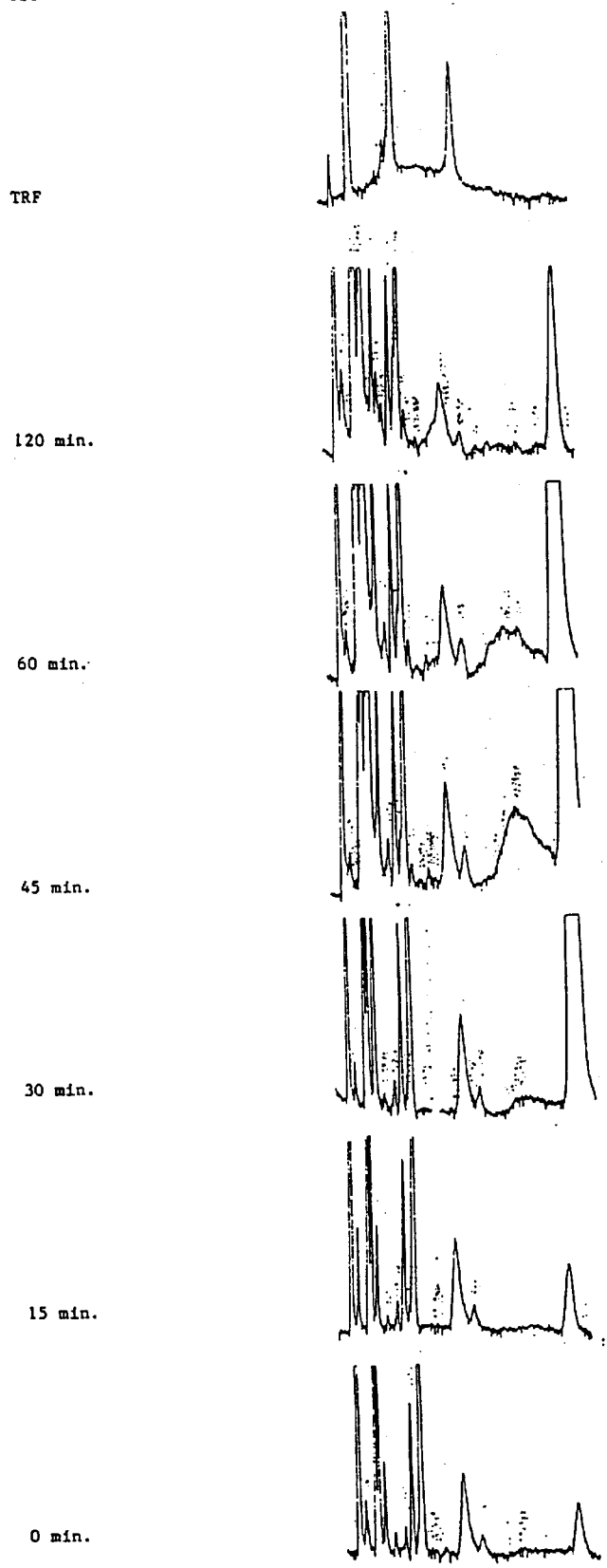
FIG. 19 shows HPLC chromograms for Rice Kernel stabilized at 180° C. for 0 minutes, 15 minutes, 30 minutes, 45 minutes, 60 minutes, and 120 minutes, with the TRF chromatogram as a control.

Using a similar experimental design, Rice Kernel was stabilized at 180° C. for 0 minutes, 15 minutes, 30 minutes, 45 minutes, 60 minutes, and 120 minutes. A TRF was used as a control. The product was extracted to yield a solvent mixture, the solvent mixture was evaporated to yield an oil, and the oil was redissolved in hexane for HPLC. The resulting HPLC chromatograms are shown in FIG. 19.

Although the foregoing invention has been described in some detail by way of illustration and example for purposes of clarity of understanding, it will be obvious that certain changes and modifications may be practiced which will still fall within the scope of the appended claims.

We claim:

1. A process for enhancing the content of recoverable Tocol products in a plant source containing significant amounts of Tocol products and for obtaining a Tocol-rich oil, comprising the steps of:
    dry heating said plant source at a temperature of from about 80° C. to about 150° C. for a period of time from about 30 minutes to about 4 hours;
    extracting the plant source with a solvent to obtain an oil-solvent mixture;
    removing solvent from said mixture to obtain a Tocol-rich oil; and,
    recovering Tocol products from said Tocol-rich oil.

2. A process for enhancing the content of recoverable Tocol products in a plant source containing significant amounts of Tocol products and for obtaining a Tocol-rich oil, comprising the steps of:
    dry heating said plant source at from about 150° C. to about 250° C. for from about 5 minutes to about 4 hours;
    extracting the plant source with a solvent to obtain an oil-solvent mixture;
    removing solvent from said mixture to obtain a Tocol-rich oil; and,
    recovering Tocol products from said Tocol-rich oil.

3. A process for enhancing the content of recoverable Tocol products in a plant source containing significant amounts of Tocol products and for obtaining a Tocol-rich oil, comprising the steps of:
    dry heating said plant source at from 200° C. to about 350° C. for 30 seconds to about 4 hours;
    extracting the plant source with a solvent to obtain an oil-solvent mixture;
    removing solvent from said mixture to obtain a Tocol-rich oil; and,
    recovering Tocol products from said Tocol-rich oil.

4. A process for enhancing the content of recoverable Tocol products in a plant source containing significant amounts of Tocol products and for obtaining a Tocol-rich oil, comprising the steps of:
    dry heating said plant source at 250° C. to about 500° C. for from about 1 second to about 90 seconds;
    extracting the plant source with a solvent to obtain an oil-solvent mixture;
    removing solvent from said mixture to obtain a Tocol-rich oil; and,
    recovering Tocol products from said Tocol-rich oil.

5. A process for enhancing the content of recoverable Tocol products in a plant source containing significant amounts of Tocol products and for obtaining a Tocol-rich oil, comprising the steps of:
    dry heating said plant source at from 180° C. to about 250° C. for from 40 seconds to about 5 minutes;
    extracting the plant source with a solvent to obtain an oil-solvent mixture;
    removing solvent from said mixture to obtain a Tocol-rich oil; and,
    recovering Tocol products from said Tocol-rich oil.

6. The process of claim 1, 2, 3, 4 or 5 wherein Tocol products are recovered from the oil by subjecting the Tocol-rich oil to refining techniques.

7. The process of claim 6 wherein said refining technique comprises low pressure, high temperature vacuum distillation.

8. The process of claim 1, 2, 3, 4 or 5 wherein the Tocol products are recovered from the oil by subjecting the Tocol-rich oil to reduced-pressure molecular distillation.

9. The process of claim 1, 2, 3, 4 or 5 wherein following dry heating the plant source is further subjected to wet heating at a temperature of from about 100° C. to about 150° C. and a pressure of between about 0 atm and about 681 atm for from about 10 seconds to about 4 hours.

10. The process of claim 1, 2, 3, 4 or 5 wherein said dry heating is carried out in an apparatus selected from the group consisting of extruders, microwaves, polarized microwaves, heating ovens, and cookers.

11. The process of claim 1, 2, 3, 4 or 5 wherein said dry heating is carried out under an inert gas, superheated steam, or a vacuum.

12. The process of claim 1, 2, 3, 4 or 5 or wherein said solvent is selected from the group consisting of propane, butane, hexane and mixtures thereof.

13. The process of claim 1, 2, 3, 4 or 5 wherein the plant source is selected from the group consisting of cereal grains, cereal grain oils, cereal bran, leaves, stems, bark, roots, legumes, and nuts.

14. The process of claim 1, 2, 3, 4 or 5 or wherein the plant source is selected from the group consisting of oats, oat bran, barley, barely bran, rice, and rice bran.

15. The process of claim 1, 2, 3, 4 or 5 further comprising the step of separating from the recovered Tocol products a Tocotrienol-rich fraction.

* * * * *